(12) United States Patent
Cimenser et al.

(10) Patent No.: US 10,660,570 B2
(45) Date of Patent: May 26, 2020

(54) ATTENTION, COMPREHENSION, AND DROWSINESS MONITORING VIA HEAD MOUNTED DEVICE SUPPORTING AUGMENTED AND MIXED REALITY EXPERIENCES

(71) Applicant: DAQRI, LLC, Los Angeles, CA (US)

(72) Inventors: Aylin Cimenser, Santa Monica, CA (US); Hani Awni, Riverwoods, IL (US)

(73) Assignee: DAQRI, LLC, Los Angeles, CA (US)

( * ) Notice: Subject to any disclaimer, the term of this patent is extended or adjusted under 35 U.S.C. 154(b) by 212 days.

(21) Appl. No.: 15/807,026

(22) Filed: Nov. 8, 2017

(65) Prior Publication Data
US 2018/0184974 A1  Jul. 5, 2018

Related U.S. Application Data

(60) Provisional application No. 62/441,219, filed on Dec. 31, 2016.

(51) Int. Cl.
| | | |
|---|---|---|
| A61B 5/00 | (2006.01) | |
| A61B 5/0482 | (2006.01) | |
| A61B 5/0478 | (2006.01) | |
| A61B 3/14 | (2006.01) | |
| A61B 5/048 | (2006.01) | |
| A61B 5/16 | (2006.01) | |
| G06T 11/60 | (2006.01) | |
| G06F 3/01 | (2006.01) | |
| A61B 5/04 | (2006.01) | |
| A61B 5/0484 | (2006.01) | |
| G06F 1/16 | (2006.01) | |
| A61B 3/113 | (2006.01) | |

(52) U.S. Cl.
CPC .............. *A61B 5/6803* (2013.01); *A61B 3/14* (2013.01); *A61B 5/048* (2013.01); *A61B 5/04012* (2013.01); *A61B 5/0478* (2013.01); *A61B 5/0482* (2013.01); *A61B 5/04845* (2013.01); *A61B 5/163* (2017.08); *A61B 5/165* (2013.01); *A61B 5/7405* (2013.01); *A61B 5/7445* (2013.01); *G06F 1/163* (2013.01); *G06F 3/011* (2013.01); *G06F 3/013* (2013.01); *G06F 3/015* (2013.01); *G06T 11/60* (2013.01); *A61B 3/113* (2013.01)

(58) Field of Classification Search
CPC ... A61B 5/6803; A61B 5/6814; A61B 5/0482; A61B 5/0476; A61B 5/0478; A61B 5/0402; A61B 5/7405; A61B 5/744; A61B 5/7445; A61B 5/165; G06F 1/163; G06F 3/013; G06F 3/015; G06T 19/006
See application file for complete search history.

(56) References Cited

U.S. PATENT DOCUMENTS

2016/0077547 A1* 3/2016 Aimone .................. A61B 5/165
345/8

* cited by examiner

*Primary Examiner* — Eric F Winakur
(74) *Attorney, Agent, or Firm* — Schwegman Lundberg & Woessner, P.A.

(57) ABSTRACT

A head mounted display (HMD) system includes an HMD device worn on a head of a user. The HMD device incorporates electroencephalography (EEG) interfaces for monitoring the brain of a human subject during interaction with the HMD device. Fluctuations in electrical potential that are observed via the EEG interfaces may be used to detect event-related potentials (ERPs). The HMD system may programmatically perform one or more operations in response to detecting ERPs. The HMD system may further include off-board devices that communicate with the HMD device over a wireless communications network.

20 Claims, 11 Drawing Sheets

ATTENTION, COMPREHENSION, AND DROWSINESS MONITORING VIA HEAD MOUNTED DEVICE SUPPORTING AUGMENTED AND MIXED REALITY EXPERIENCES

RELATED APPLICATION

This application claims the benefit of priority of U.S. Provisional Application No. 62/441,219, filed Dec. 31, 2016, which is herein incorporated by reference in its entirety.

TECHNICAL FIELD

The subject matter disclosed herein generally relates to a head-mounted display (HMD) system. Specifically, the present disclosure addresses systems for monitoring attention, comprehension, and drowsiness of a user operating the head-mounted display system.

BACKGROUND

Electroencephalography (EEG) refers to a technique for monitoring electrical activity of the brain of a living organism—typically the brain of a human subject. Fluctuations in electrical potential may be observed at various locations or regions of the brain via a set of EEG interfaces that are spatially distributed relative to the subject's head. These EEG interfaces may take the form of non-invasive electrodes that are placed near or in contact with the scalp at various locations.

An event-related potential (ERP) refers to a response of the brain to a stimulus event that has been perceived by the subject. ERPs may be detected via EEG as fluctuations in electrical potential observed during a period of time following the subject's perception of the stimulus event. With respect to human subjects, temporal fluctuations in electrical potentials observed at particular locations relative to the head of the human subject and within time-locked search windows relative to onset of the stimulus event enable such ERPs to be detected and identified.

A range of ERPs, referred to as ERP components, have been experimentally observed across large populations of human subjects in a consistent manner with respect to the type of stimulus, suggesting the universality of such ERPs in humans. Many ERP components have been characterized with respect to the type of stimulus event that elicits an observable fluctuation in electrical potential, and these fluctuations have been assigned names by the scientific community within a nomenclature that enables consistent identification and discussion of the ERP components.

DETAILED DESCRIPTION

Figure 1:
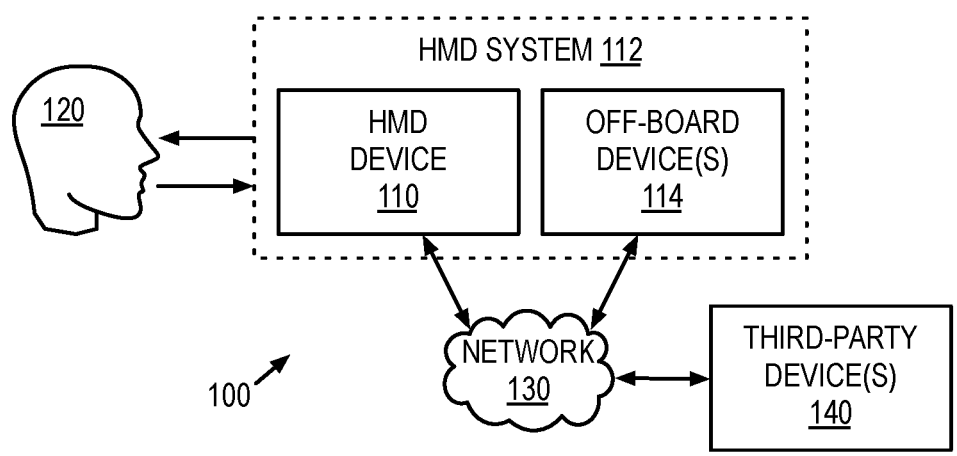
FIG. 1 is a schematic diagram depicting an example use environment that includes a head mounted display (HMD) device that is wearable by a human subject.

In accordance with an aspect of the present disclosure, a computing system presents a visual or auditory stimulus to a human subject via a head mounted device. The head mounted device may include or take the form of a head mounted display (HMD) device or other head mounted electronic device. The computing system obtains a set of one or more electroencephalography (EEG) signals via a set of spatially distributed EEG interfaces of the head mounted device. Each EEG interface includes an electrode that observes fluctuations of an electrical potential at a respective location relative to a head of the human subject.

The computing system processes the set of EEG signals to detect an event-related potential (ERP) in the subject's response to the visual or auditory stimulus by searching within the EEG signals for: (1) an ERP-P3b waveform having a positive deflection in electrical potential within an ERP-P3b time-based search window following presentation of the visual or auditory stimulus, and/or an ERP-N400 waveform having a negative deflection in electrical potential within an ERP-N400 time-based search window following presentation of the visual or auditory stimulus.

For each ERP waveform present within the set of EEG signals, the computing system measures a peak-amplitude value at the peak of that waveform and a peak-time value at the peak of that waveform relative to a time of presentation of the visual or auditory stimulus. The computing system outputs a level of drowsiness or a level of attentiveness for the human subject with respect to the stimulus based on the measurements of the peak-amplitude and the peak-time value of the ERP-P3b waveform, if present within the set of EEG signals. The computing system further outputs a level of comprehension for the human subject with respect to an information-bearing message of the stimulus based on the measurements of the peak-amplitude and the peak-time value of the ERP-N400 waveform, if present within the set of EEG signals.

The computing system may further obtain time-based imagery of an eye of the human subject via an ocular camera of the head mounted device. The computing system processes the time-based imagery to obtain measurements of eye movement with respect to the eye of the human subject. The level of drowsiness for the human subject may be further based on the measurements of eye movement.

The computing system may further process the set of EEG signals to obtain one or more of a Theta band, Alpha band, and/or Beta band, in which each band corresponds to a respective frequency range of the set of EEG signals. The level of drowsiness for the human subject may be further based on a measurement of amplitude and/or a regularity of frequency of the set of EEG signals within the one or more of the bands.

The computing system may programmatically perform one or more operations based on the level of drowsiness, the level of attentiveness, or the level of comprehension. The one or more operations may include: (1) presenting an indication of the level of drowsiness, the level of attentiveness, or the level of comprehension to the human subject via a graphical display device of the head mounted device, (2) storing the level of level of drowsiness, the level of attentiveness, or the level of comprehension in a data storage device of the head mounted device, or (3) transmitting, to another computing device over a communications network, an indication of the level of level of drowsiness, the level of attentiveness, or the level of comprehension. However, other suitable operations may be performed based on the level of drowsiness, the level of attentiveness, or the level of comprehension, as described in further detail herein.

Head mounted display (HMD) devices refer to electronic devices that feature one or more graphical display(s) and are wearable upon the head of a human subject (i.e., a user). HMD devices may include left and right near-eye graphical displays that support augmented reality (AR), mixed reality (MR), or virtual reality (VR) experiences in the visual domain. Auditory and/or haptic stimulus provided by the HMD device or associated peripheral devices may further support these visual experiences.

For HMD devices, augmented reality and mixed reality may be achieved through two primary techniques. As a first example, the near-eye graphical displays take the form of transparent display panels through which the user may view the real-world environment. Graphical content representing virtual objects may be presented on or within the transparent panels to provide the appearance of the virtual objects being physically present within the real-world environment. As a second example, the near-eye graphical displays may take the form of fully immersive display devices that occlude the user's field of vision. A camera view that approximates the user's field of vision of the real-world environment may be presented by these display devices integrated with graphical content representing virtual objects to provide the appearance of the virtual objects being physically present within the real-world environment.

FIG. 1 is a schematic diagram depicting an example use environment 100 that includes an HMD device 110 that is wearable by a human subject (i.e., a user), represented schematically at 120. HMD device 110 may include one or more graphical displays operable to visually provide an augmented reality, mixed reality, or virtual reality experience to user 120. An example HMD device is described in further detail with reference to FIGS. 10 and 11. It will be understood that HMD device 110 is a non-limiting example of a head mounted device, as other suitable head mounted devices may be used within the context of the present disclosure.

HMD device 110 may form part of an HMD system 112 that further includes one or more off-board device(s) 114. Off-board device(s) 114 may include one or more computing device(s), sensor device(s), and/or other HMD device(s), as non-limiting examples. Off-board device(s) 114 may communicate between or among each other or with HMD device 110 via a communications network 130 or a portion thereof. Communications network 130 may include one or more personal area network (PAN) components, local area network (LAN) components, and/or wide area network (WAN) components, and may support wired and/or wireless communications over one or more communications protocol(s). HMD device 110 and/or off-board device(s) 114 of HMD system 112 may communicate with one or more third-party device(s) 140 that are external the HMD system via communications network 130 or a portion thereof.

As described in further detail herein, HMD device 110 may include one or more EEG interfaces by which event-related potentials (ERPs) may be observed with respect to brain responses of a human subject. EEG refers to a technique for monitoring electrical activity of the brain of a living organism—typically the brain of a human subject. Fluctuations in electrical potential may be observed at various locations or regions of the brain via a set of EEG interfaces that are spatially distributed relative to the subject's head. These EEG interfaces may take the form of non-invasive electrodes that are placed near or in contact with the scalp at various locations.

An event-related potential (ERP) refers to a response of the brain to a stimulus event that has been perceived by the subject. ERPs may be detected via EEG as fluctuations in electrical potential observed during a period of time following the subject's perception of the stimulus event. With respect to human subjects, temporal fluctuations in electrical potentials observed at particular locations relative to the head of the human subject and within time-locked search windows relative to onset of the stimulus event enable such ERPs to be detected and identified.

A range of ERPs, referred to as ERP components, have been experimentally observed across large populations of human subjects in a consistent manner with respect to the type of stimulus, suggesting the universality of such ERPs in humans. Many ERP components have been characterized with respect to the type of stimulus event that elicits an observable fluctuation in electrical potential, and these fluctuations have been assigned names by the scientific community within a nomenclature that enables consistent identification and discussion of the ERP components. Non-limiting examples of ERPs are described in further detail with reference to FIGS. 3 and 4.

While the use of EEG is described within the context of an HMD device, it will be understood that a wearable EEG device that does not include integrated graphical displays may instead be used in combination with one or more peripheral graphical display device(s) to implement some or all aspects of the present disclosure. Within this context, the EEG device may interface with the peripheral graphical display device(s) via a communications network (e.g., 130) or a portion thereof.

Figure 2:
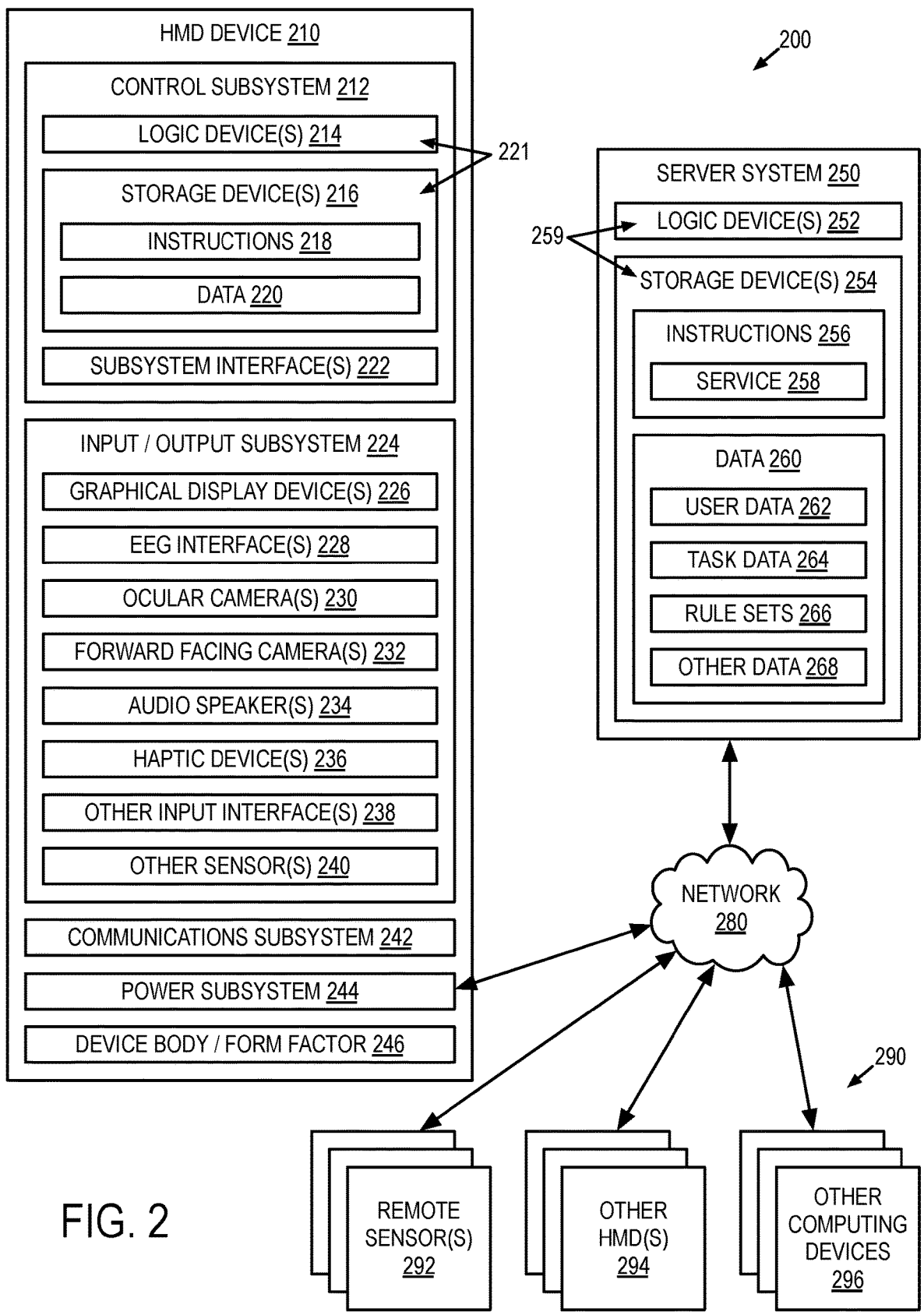
FIG. 2 is a schematic diagram depicting an example computing system that includes an HMD device.

FIG. 2 is a schematic diagram depicting an example computing system 200 that includes an HMD device 210. HMD device 210 is a non-limiting example of previously described HMD device 110 of FIG. 1, as described in further detail. Various components of HMD device 210 are represented schematically in FIG. 2. These components may be integrated with HMD device 210 or may take the form of peripheral devices that interface with HMD device 210.

HMD device 210 may include a control subsystem 212. Control subsystem 212 may include one or more logic device(s) 214, one or more storage device(s) 216, and/or one or more subsystem interface(s) 222. Storage device(s) 216 may have instructions 218 and/or data 220 stored thereon. Instructions 218 are executable by logic device(s) 214 to perform or otherwise implement the various operations, processes, functions, or tasks described herein with respect to an HMD device (or a wearable EEG device). For example, instructions 218 may define an operating system and/or on-board program that is implemented by logic device(s) of HMD device 210, enabling user interaction with the HMD device and/or the greater HMD system. Collectively logic device(s) 214 and storage device(s) 216 may take the form of an on-board computing device 221. On-board computing device 221 may be referred to as being programmed with instructions 218 when carrying instructions 218 in on-board data storage device(s) 216 and/or executing instructions 218 at logic device(s) 214.

Subsystem interface(s) 222 may operatively interface with the various other subsystems or components of HMD device 210. Subsystem interface(s) 222 may include or incorporate a computer bus, in an example, over which these various subsystems or components may communicate, share electrical power resources, or otherwise interact with each other.

HMD device 210 may further include an input/output subsystem 224, a communications subsystem 242, a power subsystem 244, and/or a device body/form factor 246. Input/output subsystem 224 may include one or more input device(s) and one or more output device(s), including as examples: one or more graphical display device(s) 226, one or more EEG interface(s) 228, one or more ocular camera(s) 230, one or more forward facing camera(s) 232, one or more audio speaker(s) 234, one or more haptic device(s) 236, one or more other input interface(s) 238, and/or other sensor(s) 240. Graphical display device(s) 226 may take the form of near-eye graphical display devices (e.g., left-eye and right-eye graphical display devices) upon which augmented reality or mixed reality content may be presented. Visual stimulus in the form of textual or non-textual graphical information may be presented to the user via graphical display device(s) 226. Auditory stimulus in the form of textual or non-textual sound information may be presented to the user via audio speaker(s) 234. Haptic stimulus representing textual or non-textual haptic information may be presented to the user via haptic device(s) 236.

Each EEG interface of EEG interface(s) 228 may include a respective electrode, associated amplifier component, associated analog-to-digital conversion component, and associated electrical power source, among other suitable components for obtaining EEG signals. Electrodes of the EEG interfaces may be passive (with sufficient contact with the human subject and/or low impedance) or active. The electrodes typically penetrate the hair of the human subject to contact the scalp or skin at respective locations relative to the head. In an example, EEG interfaces 228 may include frontal, central, and parietal EEG electrodes, among other suitable electrode locations. One or more of the EEG interfaces may include a reference electrode to which other electrodes of the EEG interfaces may be referenced. For example, one or more reference electrodes may be located at or near a mastoid, earlobe, nose tip, or other scalp location, etc. However, reference electrodes may be omitted in at least some implementations, such as with active electrodes.

Communications subsystem 242 may include one or more wireless interface devices to transmit and/or receive wireless communications. Examples of wireless interface devices include a wireless receiver, a wireless transmitter, or a wireless transceiver, as well as associated signal processing components. Wireless interface devices may support wireless communications over any suitable wireless protocol, such as Wi-Fi, Bluetooth, RFID, NFC, LTE, etc., over a personal area network, local area network, and/or wide area network components of a communications network. Wireless interface devices may utilize radio frequency and/or other suitable wireless frequency ranges, as well as electromagnetic fields in the case of RFID, to communicate wirelessly with other computing devices or electronic hardware. Communication subsystem 242 may include one or more wired interface devices. Examples of wireless interface devices include electronic connectors and associated signal processing components. Such electronic connectors may include support for exchanging an electrical ground reference, electrical power, and/or data/signal connections with a corresponding electronic connector of another device or power source.

Power subsystem 244 may include one or more on-board energy storage device(s) (e.g., a battery) for powering the HMD device and its various subsystems and components without requiring physical connection to an external power source. Power subsystem 244 may include an electronic connector for receiving electrical power from external power sources and other suitable components for providing power conditioning and distribution.

Figure 10:
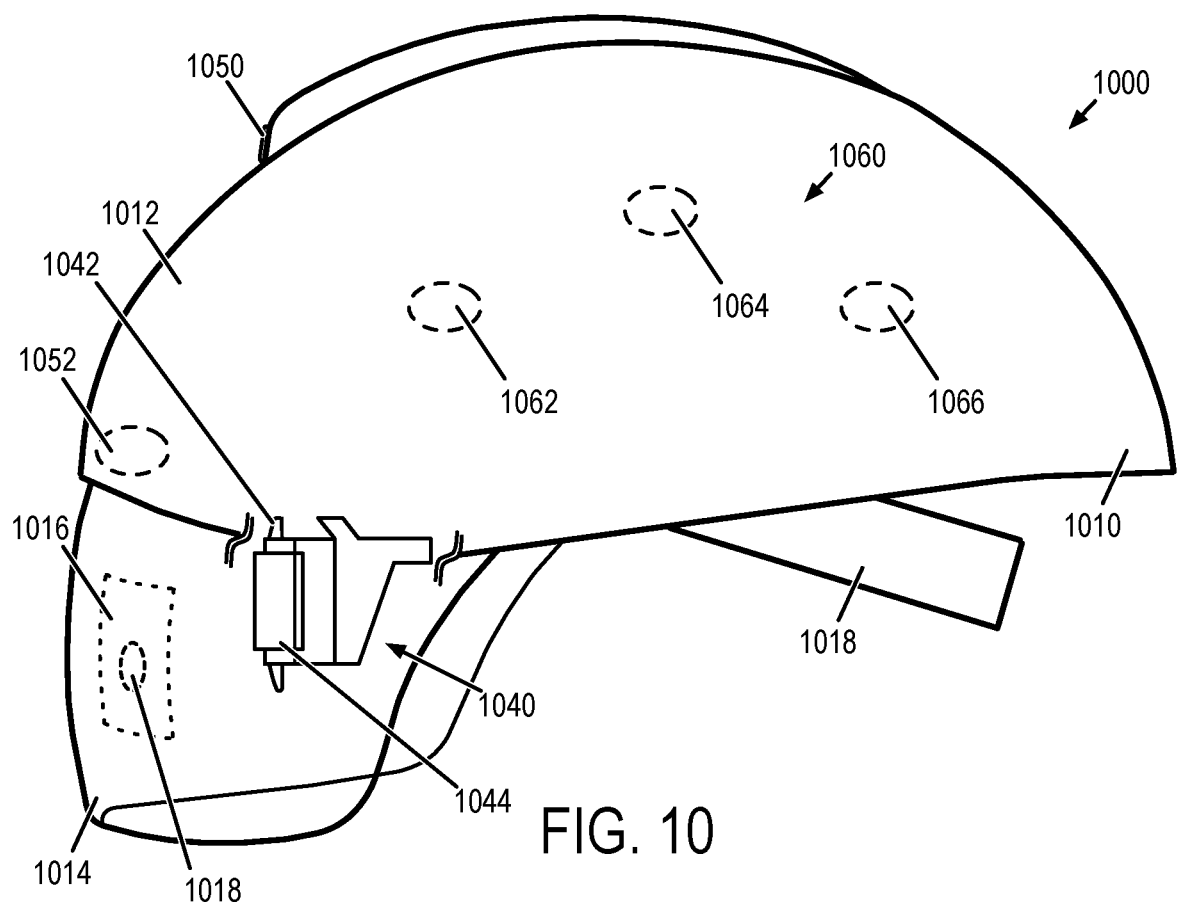
FIG. 10 depicts an example head mounted display (HMD) device that is wearable upon a head of a human subject.
Figure 11:
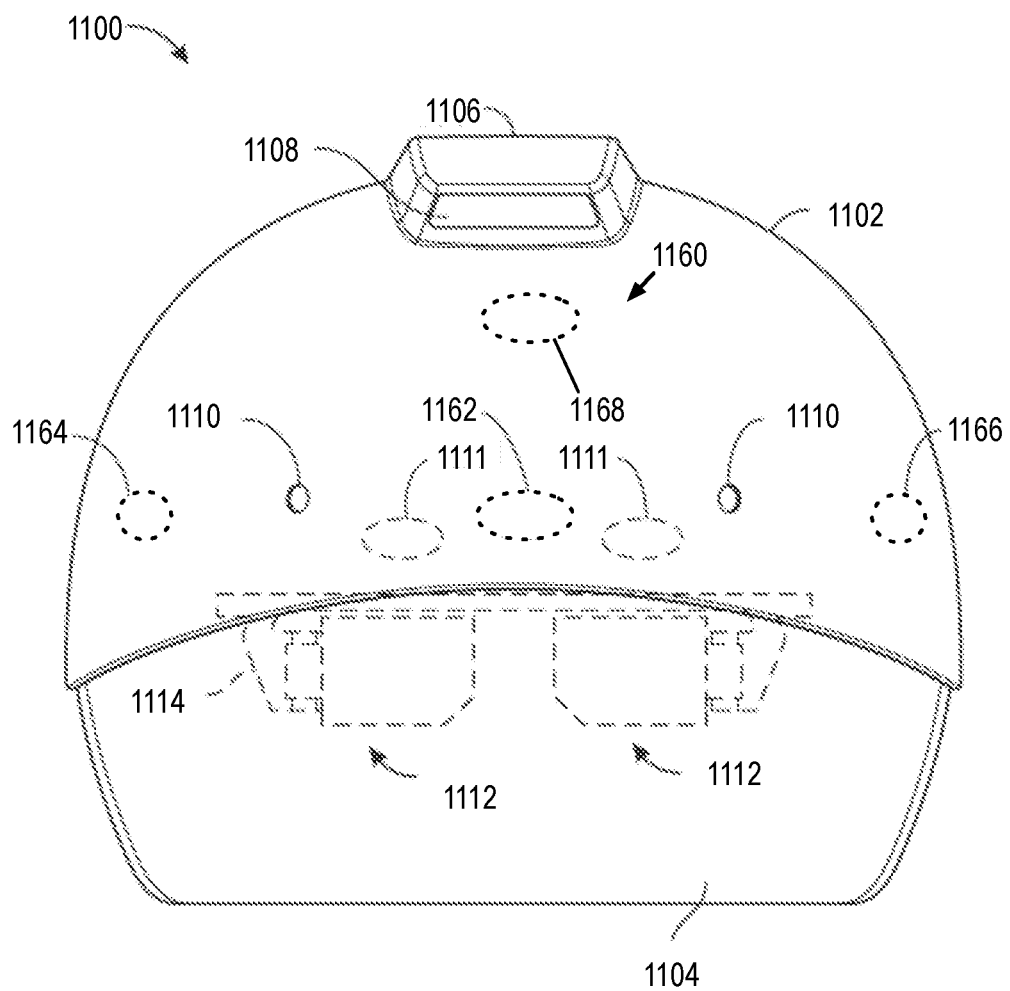
FIG. 11 depicts additional aspects of an example HMD device.

Device body/form factor 246 may include any suitable form, depending on implementation, for mounting and/or enclosing the various subsystems and components. For example, device body/form factor 246 may take the form of a helmet that is worn upon the head of a human subject, with a visor or see-through display panel that contains one or more near-eye graphical displays. FIGS. 10 and 11 depict non-limiting examples of an HMD device form factor. However, other suitable form factors may be used, depending on implementation.

Computing system 200 may further include a server system 250. Server system 250 is a non-limiting example of off-board device(s) 114 of FIG. 1. For example, server system 250 may form part of an HMD system with HMD device 210, as previously described with reference to HMD system 112 of FIG. 1. Server system 250 may include one or more server devices. Two or more server devices of server system 250 may be co-located and/or two or more server devices of server system 250 may be geographically distributed. Server system 250 may support coordinated operation with many HMD devices worn by many different users, in at least some examples.

Server system 250 may include one or more logic device(s) 252, and one or more storage device(s) 254. Storage device(s) 254 may have instructions 256 and/or data 260 stored thereon. Instructions 256 are executable by logic device(s) 252 to perform or otherwise implement the various operations, processes, functions, or tasks described herein with respect to a server system or other off-board computing device. Collectively, logic device(s) 252 and storage device(s) 254 may take the form of one or more computing device(s) 259 that are incorporated into one or more server device(s). Computing device(s) 259 may be referred to as being programmed with instructions 256 when carrying instructions 256 in data storage device(s) 254 or executing instructions 256 at logic device(s) 252.

As an example, instructions 256 may include or take the form of a program or set of programs that defines a service 258. Within the context of a networked server system, service 258 may be referred to as a hosted service or cloud-based service with which HMD 210 and/or other networked devices may communicate or otherwise interact.

For example, HMD device 210 and server system 250 may communicate via a communications network 280. Communications network 280 is a non-limiting example of previously described communications network 130 of FIG. 1. For example, communications network 280 may include wide area network components such as the Internet or a portion thereof, as well as wireless edge network components.

Examples of data 260 may include user data 262, task data 264, rule sets 266, and other data 268. User data 262 may include user profiles for users that have registered with the HMD system. Task data 264 may include task profiles for tasks that can be assigned to a user, such as within a work environment. Rule sets 266 may define operations that are to be programmatically performed by the server system or deployed to the HMD device to be performed responsive to a particular set of conditions. Other data 268 may include measurement data obtained from HMD devices, such as HMD device 210. An example data structure is described in further detail with reference to FIG. 12.

Instances of data 260 or portions thereof may reside at or may be communicated to or from other devices, such as HMD device 210. For example, instances of data included in a user profile or a task profile for a user may be distributed or otherwise made accessible to the HMD device or to a user of the HMD device, and may be temporarily or persistently stored within data 220 of storage device(s) 216 residing on-board the HMD device. Service 258 may support an access control feature that enables users to login to their respective user account of the service by providing login credentials. Following login, the service may identify a particular user as being associated with a particular HMD device. Service 258 may distinguish among many users of the service and their respective devices to support many concurrent client sessions. Service 258 may interface with on-board programs operating at HMD device 210 via an application programming interface (API) that forms part of the service or part of the on-board program.

Computing system 200 may include a variety of other devices 290, such as one or more remote sensor(s) 292, one or more other HMD(s) 294, and one or more other computing device(s) 296. Depending on implementations, some of devices 290 may be examples of third-party device(s) 140 of FIG. 1 that are external the HMD system. However, some or all of devices 290 may represent examples of off-board device(s) 114 of FIG. 1 that collectively form part of HMD system 112 with one or more HMD devices.

Within the field of EEG, the "10-20 system" defines a standardized nomenclature that describes a variety of surface locations of a human head. Within this nomenclature, various locations on the surface (e.g., scalp) of the head may be described by an alphanumeric code, which may take the form of a combination of a first character (typically a letter represented in upper case) that defines a brain lobe or other region of the head, and a second character (typically a number or a second letter represented in lower case) that defines a hemisphere or other region relative to a midline of the head. With regards to the first character, the letters F, T, C, P, O, A refer to the following regions: frontal lobe, temporal lobe, central region, parietal lobe, occipital lobe, and earlobe, respectively. With regards to the second character, even numbers (e.g., 2, 4, 6, 8) refer to respective locations on the right hemisphere of the head and odd numbers (e.g., 1, 3, 5, 7) refer to respective locations on the left hemisphere of the head. Also with regards to the second character, the letter "z" corresponding to the number "zero" or "0" refers to a location along a midline of the head. Furthermore, the code "Fp" refers to the frontal polar location of the head, and the code "Pg" refers to nasopharyngeal location.

EEG interfaces may include corresponding electrodes that are spatially distributed along the scalp or other surfaces of the head of a human subject to provide a variety of different observation points for observing fluctuations in electrical potential. For example, a set of EEG interfaces may be spatially distributed at or near locations corresponding to Fpz, Fz, Cz, etc., to use the nomenclature of the 10-20 system, among other suitable electrode locations. Fluctuations in electrical potential occurring within the head of the human subject may be observed via these spatially distributed EEG interfaces. Each observation point provides a different measurement of electrical potential that reflects brain activity of the human subject proximate to and from the perspective of that observation point.

Time-based measurements of electrical potential observed via the EEG interfaces over a period of time may be captured and analyzed to identify characteristic fluctuations in electrical potential that correspond to an event-related potential (ERP). An ERP refers to a response of the brain of a human subject that results from a sensory-based event, cognitive-based event, and/or motor-based event (collectively referred to as stimulus events). An ERP may include one or more components that are related to and identifiable from positive or negative deflections (relative to a baseline) in the electrical potential that are present in a time-based waveform that is observed at a particular observation point. Non-limiting examples of ERP components are described in further detail with reference to FIGS. 3 and 4.

Fluctuations in electrical potential observed via at last one electrode of an EEG interface may take the form of positive and/or negative deflections in electrical potential relative to a baseline. A waveform representing a deflection in electrical potential may include a beginning, an end, and a maximum value or peak located between the beginning and end of the waveform. Because the EEG signal representing the observed electrical potential is a time-varying signal, the beginning, end, and absolute maximum value may be associated with time values within a global time frame and within a time frame that is keyed to onset of the stimulus event that elicited the response. EEG signals obtained from a set of two or more EEG interfaces may be time-locked relative to each other to enable comparison of electrical potential observations between or among the EEG interfaces.

Figure 3:
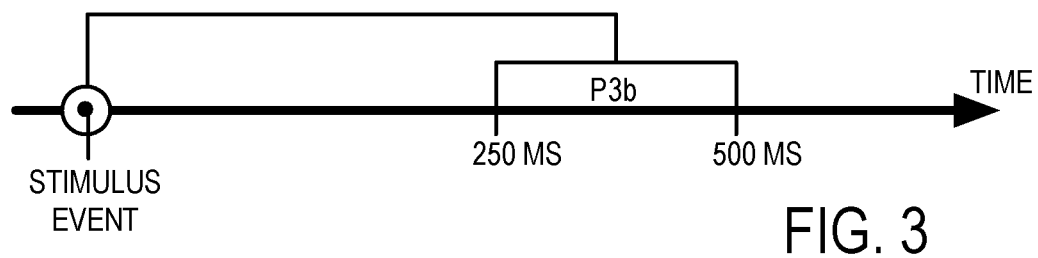
FIG. 3 is a timeline depicting an example relationship between a stimulus event and resulting fluctuations in electrical potential indicative of an ERP, including a P300/P3b (ERP-P3b) component observed via one or more EEG interface(s).

FIG. 3 is a timeline depicting an example relationship between a stimulus event and resulting fluctuations in electrical potential indicative of an ERP, including a P300/P3b (ERP-P3b) component observed via one or more EEG interface(s). The ERP-P3b component may be characterized as a waveform of a positive deflection relative to a baseline that typically has a peak amplitude approximately 250-500 milliseconds (ms) (e.g., 300 ms) subsequent to onset of the stimulus event. This time range may be referred to as an ERP-P3b search window that is time-locked to the stimulus event. As an example, the peak amplitude may be up to 20.0 microvolts within the ERP-P3b search window as compared to the pre-stimulus baseline voltage. A stimulus event used to elicit an instance of the ERP-P3b component may include a task-relevant stimulus that relies on active processing by the human subject (as opposed to passive processing characteristic of the P3a component). An example of a stimulus event suitable for eliciting the ERP-P3b component includes the presentation of superficial oddball stimulus. When a human subject is exposed to a sequence of stimuli, some of which are superficially different than the others, an ERP-P3b component will typically be elicited in response to the unusual stimulus (e.g., oddball) whose magnitude and delay are dependent on the rarity of the stimulus, the age, gender, and genetics of the user, and their current state of sleepiness, cognitive workload, attentional capacity, among other factors. The ERP-P3b component is typically observed via an electrode positioned at or near the Parietal (Pz) location relative to the head of a human subject. However, other suitable locations may be used to observe the ERP-P3b component.

Figure 4:
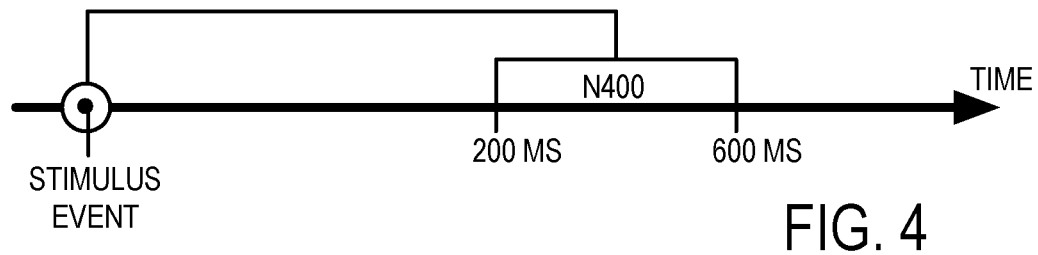
FIG. 4 is a timeline depicting an example relationship between a stimulus event and resulting fluctuations in electrical potential indicative of an ERP, including a N400 (ERP-N400) component observed via one or more EEG interface(s).

FIG. 4 is a timeline depicting an example relationship between a stimulus event and resulting fluctuations in electrical potential indicative of an ERP, including an N400 (ERP-N400) component observed via one or more EEG interface(s). The ERP-N400 component may be characterized as a waveform of a negative deflection relative to a baseline that typically has a peak amplitude approximately 200-600 ms (e.g., 400 ms) subsequent to onset of the stimulus event. This time range may be referred to as an ERP-N400 search window that is time-locked to the stimulus event. A stimulus event used to elicit an instance of the ERP-N400 component may include presentation of a semantic oddball stimulus. The ERP-N400 may be sensitive to attention and expectations associated with the human subject. The ERP-N400 component is typically observed via an electrode positioned at or near the Central-Parietal (Cz-Pz) location relative to the head of a human subject. However, other suitable locations may be used to observe the ERP-N400 component. For example, a right hemisphere bias for electrode positioning may be suitable for stimulus events that include visually perceivable written text that is readable by the human subject.

The ERP-N400 component typically occurs after onset of a stimulus that requires the reparsing of the previous sentence or message contents in order to fit into a logical structure. The classic stimuli to elicit an ERP-N400 component rely on a series of words presented one-at-a-time (e.g., within sequential image frames). A semantic incongruity occurs such that there is an anomaly among expected words, for example, "I take my coffee with cream and dog," which elicits an ERP-N400 component in response to the word "dog". However, such an absurdity is not required to elicit an ERP-N400 component. Any sentence or message which requires effort or conceptual reorganization by the human subject for understanding may elicit an ERP-N400 component. Accordingly, an ERP-N400 component may be evoked in response to semantically difficult sentences, as a grammatical or syntactic errors will typically elicit a later positivity called the P600 instead. Furthermore, repetitions of the original N400-eliciting stimulus will typically result in decaying magnitude among the ERP-N400, as the quantity of trials progress. With detection of the ERP-N400 component within an EEG signal, it becomes possible to detect when a user (e.g., of an HMD device) puts forth excess effort to comprehend a given message. This enables monitoring of comprehension with respect to whether the user actually understood a message that, in expectation, would elicit an N400 given their level of training or background.

In real-world implementations, measurements of ERP waveforms such as those representing the ERP-P3b and ERP-N400 components may vary with operating conditions, such as the type of the stimulus event, the content of the stimulus event, the sensory modality for perceiving the stimulus event, context or environmental conditions, and characteristics or conditions of the human subject (e.g., age, health, skill level/experience, etc.). Such measurements may include a size of the ERP time-based search window, a magnitude of the latency between onset of the stimulus event and observation of the ERP waveform, the amplitude of the ERP waveform, and the shape of the ERP waveform, etc. As will be described in further detail with reference to the methods of FIGS. 5, 6, and 7, user-specific training of computer-implemented ERP detection programs (e.g., classifiers) may be performed to obtain historic baseline information for an individual human subject across a variety of operating conditions. Such training may enable ERP waveforms to be detected, measured, and attributed to a level of drowsiness, attentiveness, and/or comprehension with respect to the human subject.

Figure 5:
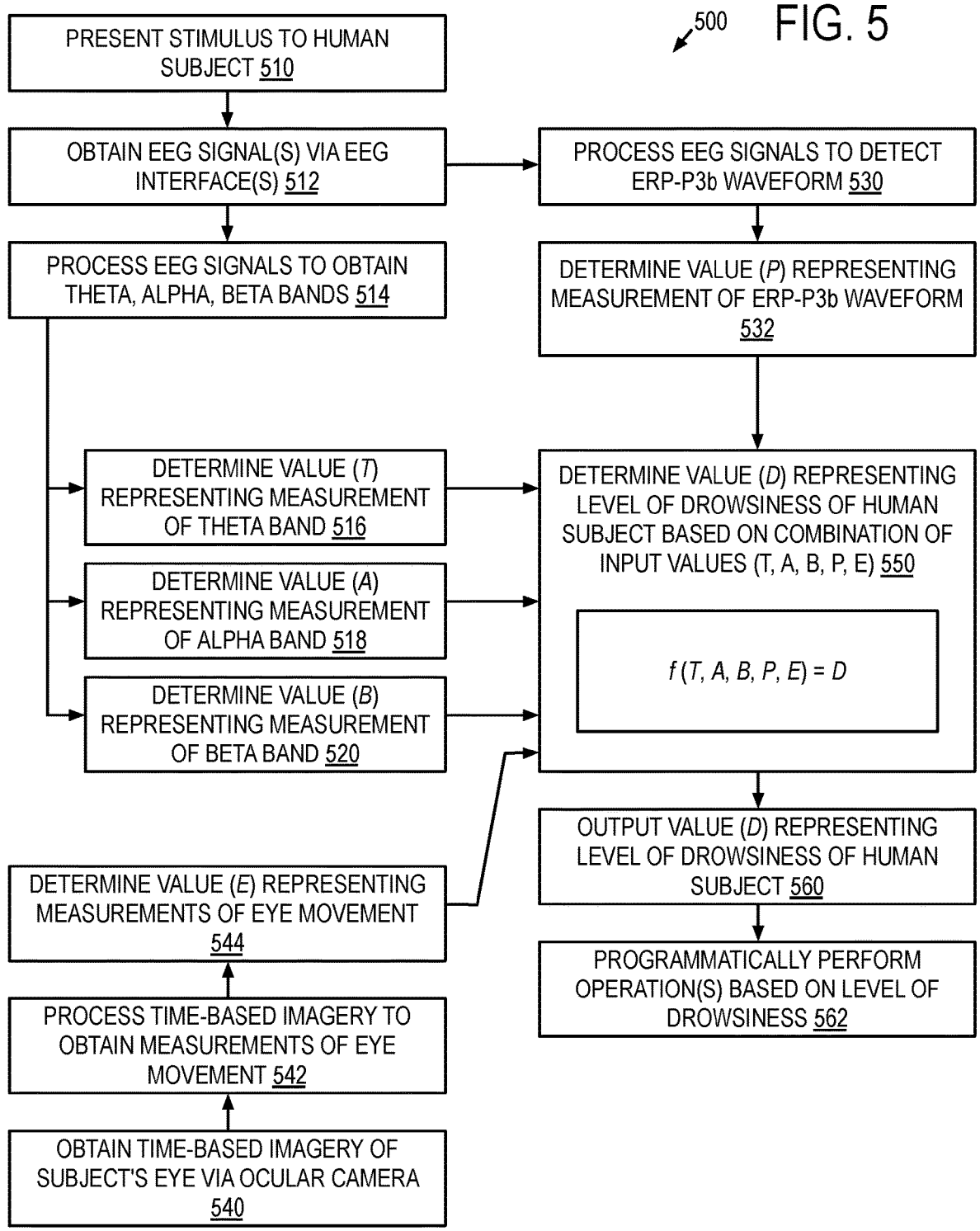
FIG. 5 is a flow diagram depicting an example method associated with drowsiness monitoring with respect to a human subject.

FIG. 5 is a flow diagram depicting an example method 500 associated with drowsiness monitoring with respect to a human subject. In at least some implementations, method 500 or portions thereof may be performed by a computing device located on-board an HMD device. Alternatively or additionally, portions of method 500 may be performed off-board the HMD device by one or more off-board computing devices of the HMD system. Furthermore, in at least some implementations, method 500 or portions thereof may be performed in real-time, and during runtime of the HMD device with respect to the human subject as a user of the HMD device. However, in other implementations, portions of method 500 may be performed in a post-processing operation that is not necessarily in real-time or during runtime of the HMD device. Method 500 may be performed in combination with methods 600 and/or 700 of FIGS. 6 and 7 to achieve more robust monitoring of drowsiness, attention, and comprehension with respect to a human subject.

Within method 500, the HMD system obtains input data associated with a human subject, including the following components: (1) Theta, Alpha, and Beta bands within one or more EEG signals, (2) ERP-P3b observation data within one or more EEG signals, and (3) eye movement data captured via an ocular camera. These components of the input data may be factors that influence a level of drowsiness determined by the HMD system for the human subject.

At 510, the method includes presenting a stimulus to the human subject. The stimulus may be selected to elicit an ERP-P3b component from the human subject. The stimulus may include visual, auditory, and/or haptic components that are presented via an HMD device or other suitable EEG device of the HMD system worn by the human subject. Method 600 of FIG. 6 describes additional aspects of stimuli that may be used within the context of eliciting ERP-P3b responses from a human subject. Briefly, an instance of the ERP-P3b component may be detected in a EEG signal in response to an oddball paradigm (e.g., repetitive sounds are presented with infrequent interruptions of deviant stimuli; i.e. oddball) in which changes in latency and amplitude of the oddball may be detected after 300 msec, as a non-limiting example.

At 512, the method includes obtaining a set of one or more EEG signals via a set of one or more EEG interfaces. The set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, sampling, and storing or otherwise buffering the signal information in a data storage device (e.g., as sampled data). In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 514, the method includes processing one or more of the EEG signals to obtain Theta, Alpha, and Beta bands. One or more of the EEG signals may be processed by selective filtering based on signal frequency to obtain one or more frequency ranges or bands, respectively. Neural oscillation (e.g., rhythmic activity) observed within an individual band may correspond to a particular biological response or state of a human subject. For example, bands obtained from the EEG signals may include the Theta, Alpha, and Beta bands. For each band, relative low frequency power to total power may be detected and then associated with drowsiness.

The Theta band may refer to a frequency range of approximately 4 Hz to approximately 8 Hz. However, other suitable ranges for the Theta band may be used. Neural oscillation of a particular characteristic within the Theta band may correspond to drowsiness in a human subject. At 516, the method includes determining a value (T) representing a measurement of the Theta band. In at least some implementations, the measurement of the Theta band may be based on an amplitude value (e.g., maximum voltage value, average voltage value, degree of change in voltage between oscillations, etc.) in the amplitude/voltage domain and/or a measurement of the oscillation (e.g., frequency, frequency range, wavelength, wavelength range, regularity of frequency, etc.) in the time domain. The measurement of the Theta band may alternatively or additionally be based on comparison of the EEG signal within the Theta band to a Theta-baseline. The Theta-baseline may be pre-defined and/or based on historic measurements of the Theta band with respect to the human subject or other subjects within a group of users. Historic measurements of the Theta band may be obtained during a training phase involving the human subject or other subjects, and/or during runtime within real-world implementations involving the human subject or other subjects. The Theta-baseline may be developed with respect to a particular set of operating conditions (e.g., time of day, context, etc.) and/or human state (e.g., drowsy or non-drowsy). Furthermore, in at least some implementations, the value (T) may instead take the form of two, three, or more separate values (e.g., T1, T2, T3, etc.) that correspond to respective measurements of the Theta band rather than an individual combined value (T).

The Alpha band refers to a frequency range of approximately 7.5 Hz to approximately 15 Hz. However, narrower ranges for the Alpha band may include approximately 8 Hz to approximately 12.5 Hz. Neural oscillation within the Alpha band of a particular characteristic within the Alpha band may correspond to a relaxed state or a drowsy state in a human subject. For example, neural oscillation having relatively low amplitude may correspond to a relaxed state or drowsy state. However, the Alpha band may be sensitive to whether the eyes are open or closed. Accordingly, measurements of the open/closed state of the eyes may further inform the extent to which the Alpha band measurements indicate a relaxed state or drowsy state. At 518, the method includes determining a value (A) representing a measurement of the Alpha band. In at least some implementations, the measurement of the Alpha band may be based on an amplitude value (e.g., maximum voltage value, average voltage value, degree of change in voltage between oscillations, etc.) in the amplitude/voltage domain and/or a measurement of the oscillation (e.g., frequency, frequency range, wavelength, wavelength range, regularity of frequency, etc.) in the time domain. The measurement of the Alpha band may alternatively or additionally be based on comparison of the EEG signal within the Alpha band to an Alpha-baseline. The Alpha-baseline may be pre-defined and/or based on historic measurements of the Alpha band with respect to the human subject or other subjects within a group of users. Historic measurements of the Alpha band may be obtained during a training phase involving the human subject or other subjects, and/or during runtime within real-world implementations involving the human subject or other subjects. The Alpha-baseline may be developed with respect to a particular set of operating conditions (e.g., time of day, context, task, stimulus, etc.) and/or human state (e.g., drowsy or non-drowsy). Furthermore, in at least some implementations, the value (A) may instead take the form of two, three, or more separate values (e.g., A1, A2, A3, etc.) that correspond to respective measurements of the Alpha band rather than an individual combined value (A).

The Beta band refers to a frequency range of approximately 12.5 Hz to approximately 32 Hz. However, narrower ranges for the Beta band may include approximately 14 Hz to approximately 30 Hz. Neural oscillation within the Beta band having relatively low amplitude and multiple varying frequencies may correspond to an active and/or alert state in the human subject, for example. At 520, the method includes determining a value (B) representing a measurement of the Beta band. In at least some implementations, the measurement of the Beta band may be based on an amplitude value (e.g., maximum voltage value, average voltage value, degree of change in voltage between oscillations, etc.) in the amplitude/voltage domain and/or a measurement of the oscillation in the time domain (e.g., frequency, frequency range, wavelength, wavelength range, regularity of frequency, etc.). The measurement of the Beta band may alternatively or additionally be based on comparison of the EEG signal within the Beta band to a Beta-baseline. The Beta-baseline may be pre-defined and/or based on historic measurements of the Beta band with respect to the human subject or other subjects within a group of users. Historic measurements of the Beta band may be obtained during a training phase involving the human subject or other subjects, and/or during runtime within real-world implementations involving the human subject or other subjects. The Beta-baseline may be developed with respect to a particular set of operating conditions (e.g., time of day, context, task, stimulus, etc.) and/or human state (e.g., drowsy or non-drowsy). Furthermore, in at least some implementations, the value (B) may instead take the form of two, three, or more separate values (e.g., B1, B2, B3, etc.) that correspond to respective measurements of the Beta band rather than an individual combined value (B).

At 530, the method includes processing one or more of the EEG signals of the set to detect an ERP-P3b waveform. For example, an EEG signal may be obtained via at least one EEG interface having an electrode that observes the temporal-parietal regions of the head of the human subject. The ERP-P3b waveform may be detected within an ERP-P3b search window of the EEG signal approximately 250-500 ms following onset of the stimulus event presented at operation 510. In at least some implementations, the largest amplitude of a positive deflection occurring within this ERP-P3b search window may be identified as the peak of the ERP-P3b waveform. The ERP-P3b waveform may be sampled, stored, and analyzed as sub-processes to operation 530.

Following detection of the ERP-P3b waveform, a waveform profile may be established in a database system that represents an association between or among a variety of information relating to the waveform event. As a non-limiting example, an association may be established between some or all of the following information with regards to a detected ERP-P3b waveform: (1) a waveform event identifier that is sufficiently unique within a domain to enable a particular instance of a detected ERP waveform to be distinguished from other instances of detected ERP waveforms with respect to the human subject and/or among other human subjects of a group, (2) sampling data obtained from the EEG signal representing the waveform and/or data surrounding the waveform within a buffer region (e.g., voltage values vs. time values describing the waveform), (3) baseline data obtained from the EEG signal representing a baseline voltage prior to onset of the stimulus and/or between onset of the stimulus and the beginning of the waveform deflection, (4) a peak-amplitude value (e.g., maximum voltage value) at the peak of the waveform (e.g., measured relative to the baseline or other reference value), (5) a peak-time value at the peak of the waveform (e.g., measured relative to the onset of stimulus event) or other suitable measure of latency of the waveform in relation to onset of the stimulus event, (6) a trial number for the stimulus event within a set of stimulus events presented to the human subject during the current session for eliciting the ERP-P3b component and/or across all sessions for the human subject, (7) a wavelength or time-based measurement of the waveform within the time domain, (8) an average magnitude or integral of the waveform, (9) a measurement of the degree of symmetry of the waveform about the peak-amplitude value within the voltage and/or time domains, among other suitable data.

At 532, the method includes determining a value (P) representing a measurement of the ERP-P3b waveform detected at 530. In at least some implementations, the value (P) may be determined based on a comparison of the ERP-P3b waveform to a P3b-baseline. As a non-limiting example, the value (P) may be based on a combination of measurements obtained at operation 530, including (1) the peak-amplitude value (e.g., maximum voltage value) at the peak of the waveform (e.g., measured relative to the baseline or other reference value), (2) the peak-time value at the peak of the waveform (e.g., measured relative to the onset of stimulus event) or other suitable measure of latency of the waveform in relation to onset of the stimulus event, (3) a trial number for the stimulus event within a set of stimulus events presented to the human subject during the current session for eliciting the ERP-P3b component and/or across all sessions for the human subject. Accordingly, the value (P) may represent a multi-dimensional set of two, three, or more measurements. However, the value (P) may be based on other suitable combinations of measurements of the waveform as compared to P3b-baseline.

As described in further detail with reference to FIG. 6, the P3b-baseline may be pre-defined and/or based on historic measurements of ERP-P3b waveforms with respect to the human subject or other subjects within a group of users. Historic measurements of ERP-P3b waveforms may be obtained during a training phase involving the human subject or other subjects, and/or during runtime within real-world implementations involving the human subject or other subjects. The P3b-baseline may be developed with respect to a particular set of operating conditions (e.g., time of day, context, task, stimulus, etc.) and/or human state (e.g., drowsy or non-drowsy). As a non-limiting example, increase in latency and decrease in amplitude of the ERP-P3b waveform relative to the P3b-baseline may be associated with drowsiness in the human subject. Instead of single amplitude and latency measures, evolution of each ERP-P3b waveform may be examined between awake and drowsy states of the human subject. Baseline measurements may be obtained when the human subjects are in a fully awake state, which may be inferred from time of day and/or may be user-defined by a user input to the HMD device or HMD system. A cluster of P3b waveform data for the awake state may be characterized. Deviations from this cluster may be explored in different conditions. Drowsiness levels may be mapped for an individual human subject or a generalized human subject. Future ERP-P3b waveform values may be compared to these baseline measurements to determine the level of drowsiness. Furthermore, in at least some implementations, the value (P) may instead take the form of two, three, or more separate values (e.g., P1, P2, P3, etc.) that correspond to respective measurements of the ERP-P3b waveform, such as the peak-amplitude value, the peak-time value, and the trial number for the stimulus event rather than an individual combined value (P).

At 540, the method includes obtaining time-based imagery of an eye of the human subject via an ocular camera. The ocular camera captures time-based imagery (e.g., a video) of the eye of the human subject. Image data representing a sequence of image frames of the time-based imagery is obtained from the ocular camera. Each image frame may have an associated timestamp that represents a time at which the image frame was captured.

At 542, the method includes processing the time-based imagery to obtain measurements of eye movement for the human subject. Movement associated with the eye may be identified between two or more individual image frames of the time-based imagery. Movement associated with the eye may include: (1) rotation of the eye, (2) change in size of the pupil due to dilation, (3) opening or closing of the eyelids and/or associated features of the eyelids. For each image frame, a value representing an orientation of the eye, a value representing a size of the pupil, and/or a value representing a relative positioning of the eyelids may be determined and assigned to the image frame or a timestamp associated with the image frame. In at least some implementations, a variety of computer vision techniques may be applied to the image frames to identify and measure features of the eye and surrounding structure. These computer vision techniques may also be utilized on-board the HMD device within the context of real-time eye tracking for determining a gaze vector and user selection of objects present within a field of view of the user, as described in further detail with reference to FIG. 9.

Movement associated with the eye may be identified by a difference in orientation of the eye, size of the pupil, and/or relative positioning of the eyelids between at least two image frames. A value representing such movement of the eye, pupil, or eyelids between two image frames may also be assigned a corresponding direction to obtain a vector representing a magnitude and direction of the movement. These two image frames may be sequential or non-sequential within the time-based imagery. A rate of movement associated with the eye may be identified by dividing the difference in values between two image frames by a time difference between the timestamps of the two image frames. A rate of movement identified from multiple pairs of image frames may be compared to identify a rate of change of such movement over a period of time represented by the image frames.

An orientation of the eye may be within a three degree-of-freedom (3DOF) reference frame having corresponding yaw, pitch, and roll values within a coordinate system. Eye rotation may be may be identified as a change in one or more of the yaw, pitch, and roll values that describe a change in orientation of the eye between two instances in time. The orientation of the eye may be identified by comparing a feature of the eye to a light-based glint formed on a surface of the eye. This light-based glint may represent a reflection of light from a fixed light source (e.g., an infrared emitter mounted to the wearable device).

A size of the pupil may be characterized by a measured value of a linear dimension (e.g., a radius or diameter), an area, or a circumference. A change in the size of the pupil may be identified as a change in a value of the linear dimension, area, or circumference between two instances in time.

A position of the upper and/or lower eyelids may be characterized with respect to each other, with respect to the eye, with respect to other physical features of the subject's face, or with respect to a light-based glint formed on a surface of the eye. A linear dimension (e.g., a distance) from the upper eyelid to the lower eyelid or an area bounded by the upper eyelid and lower eyelid through which the eye is visible may be used to describe a relative position of the upper eyelid relative to the lower eyelid. A position of either eyelid may also be measured as a linear dimension from the outer edge the eyelid to a physical feature of the subject's face or eye (assuming orientation of the eye remains relatively fixed). A light-based glint on the surface of the eye, representing a reflection of light from a fixed light source (e.g., an infrared emitter mounted on a wearable device) may serve as a reference from which a position of the upper and/or lower eyelids may be measured, such as by a linear dimension. An opening or closing of the eyelids may be identified as a change in value of the linear dimension or area between two instances in time.

At 544, the method includes determining a value (E) representing the measurements associated with the eye movement for the human subject. The value (E) may be based on measurements of movement for one or more of the eye, pupil, or eyelids. In at least some implementations, the value (E) may be determined based on a comparison of the measurements associated with the eye movement to an eye movement-baseline. The eye movement-baseline may be pre-defined and/or based on historic measurements of eye movement with respect to the human subject or other subjects within a group of users. For example, slowing eye movements of the human subject over time may be associated with drowsiness or an increasing level of drowsiness. Historic measurements of eye movement may be obtained during a training phase involving the human subject or other subjects, and/or during runtime within real-world implementations involving the human subject or other subjects. The eye movement-baseline may be developed with respect to a particular set of operating conditions (e.g., time of day, context, task, stimulus, etc.) and/or human state (e.g., drowsy or non-drowsy). Furthermore, in at least some implementations, the value (E) may instead take the form of two, three, or more separate values (e.g., E1, E2, E3, etc.) that correspond to respective measurements of eye movement rather than an individual combined value (E).

At 550, the method includes determining a value (D) representing a level of drowsiness of the human subject based on a combination of input values (T), (A), (B), (P), (E). The HMD system may implement a logic module configured to determine a level of drowsiness based on the specific values of the input data. For example, the value (D) may be represented as a function of the input values: f (T, A, B, P, E)=D. This function may take a variety of different forms. For example, the value (D) may represent an average or other filtered combination of input values (T), (A), (B), (P), and/or (E), among other suitable input values. However, in other implementations some of the input values may be omitted as factors for determining the value (D). For example, input values for one or more of the Theta, Alpha, or Beta bands may be omitted as factors. As another example, input values for eye movement may be omitted as a factor. In at least some implementations, these input values may be scaled within respective ranges prior to being combined to obtain the value (D). Furthermore, in at least some implementations, a weighting may be assigned to each of the input values that is based on a confidence of the underlying data of the input values (e.g., an age of the underlying data or a signal-to-noise ratio of the underlying data).

At 560, the method includes outputting the value (D) representing a level of drowsiness of the human subject. The value (D) may be one of a plurality of values within a domain of potential values for (D). This domain of potential values may include a plurality of discrete values or a continuous range of values, each representing a respective level of drowsiness. For example, a domain of potential drowsiness levels may have at least two levels (i.e., binary) represented by two distinguishable values (e.g., 0,1) that correspond to a less drowsy state and a more drowsy state, respectively. Three or more levels may be represented by respective values within the domain of potential values for (D). Each pair of neighboring values for (D) within the domain of potential values may be delineated by a threshold, at least within the context of discrete values representing discrete levels of drowsiness.

At 562, the method includes programmatically performing one or more operations based on the value (D) representing the level of drowsiness of the human subject. In at least some implementations, the HMD system may implement a rule set that defines a relationship between a domain of two or more potential values or value ranges for the value (D) representing the level of drowsiness, and a set of operations to be programmatically performed by the HMD system. In this example, for a given value (D) or value range containing the value (D), the rule set defines one or more respective operations to be programmatically performed by the HMD system. Accordingly, the HMD system may respond differently depending on the level of drowsiness determined for the user at a given point in time. Examples of operations that may be programmatically performed by the HMD system are described in further detail with reference to FIG. 8. Method 500 or portions thereof may be performed periodically or at defined time intervals to obtain updated measurements of the human subject and determine an updated level of drowsiness associated with the human subject.

Figure 6:
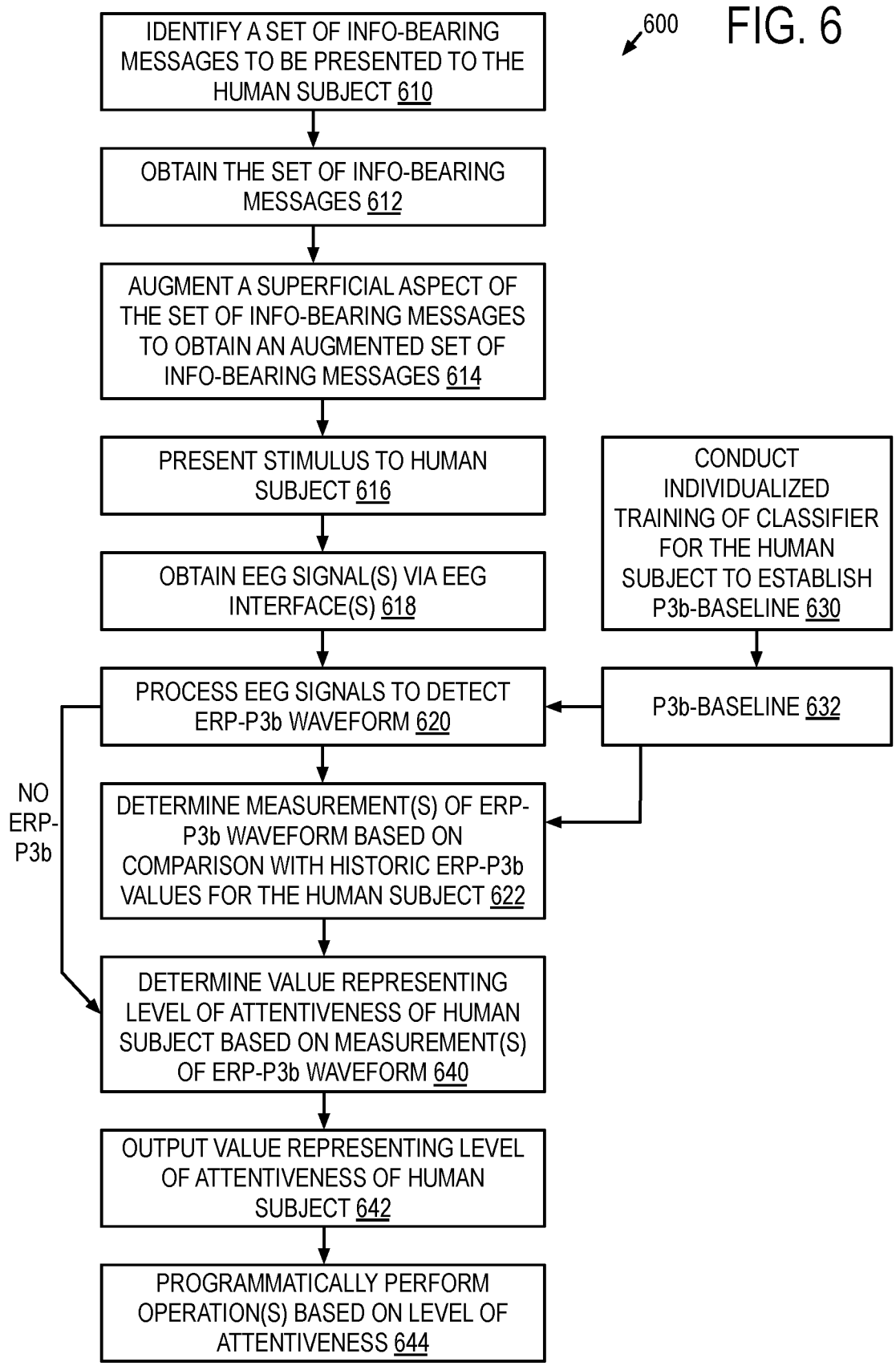
FIG. 6 is a flow diagram depicting an example method associated with attention monitoring with respect to a human subject.

FIG. 6 is a flow diagram depicting an example method 600 associated with attention monitoring with respect to a human subject. Method 600 may be used to track a user's daily variation in attentiveness level due to Circadian rhythm so that their work-related tasks can be better scheduled according to their estimated instantaneous maximum attentional capacity or sufficient attentional capacity for each particular task. This allows the HMD device or HMD system to be more aware of and responsive to the needs of the user in the immediate and long term pursuit of a more harmonious neurodigital synthesis.

In at least some implementations, method 600 or portions thereof may be performed by a computing device located on-board an HMD device. Alternatively or additionally, portions of method 600 may be performed off-board the HMD device by one or more off-board computing devices of the HMD system. Furthermore, in at least some implementations, method 600 or portions thereof may be performed in real-time, and during runtime of the HMD device with respect to the human subject as a user of the HMD device. However, in other implementations, portions of method 600 may be performed in a post-processing operation that is not necessarily in real-time or during runtime of the HMD device. Method 600 may be performed in combination with methods 500 and/or 700 of FIGS. 5 and 7 to achieve more robust monitoring of drowsiness, attention, and comprehension with respect to a human subject.

At 610, the method includes identifying a set of information-bearing messages to be presented to the human subject. This set of messages may be identified for a given context of the user (i.e., the human subject) and/or client device (e.g., the HMD device) within an active session, which may be based on the operating conditions and/or the operating mode identified by the HMD system. The set of messages may include one or more information-bearing messages. Such messages may be generated by the HMD system or the HMD device, or may be received from a third-party device.

At 612, the method includes obtaining the set of information-bearing messages. Each information-bearing message of the set of message may include one or more human-perceivable sentences, sentence fragments, phrases, or words that contain text-based information reproducible in either visual or auditory form. Each message may be obtained by retrieving the message from a data storage device or receiving the message from another device over a communications network.

At 614, the method includes augmenting a superficial aspect of the set of information-bearing messages to obtain an augmented set of information bearing messages. For text-based message components (e.g., words, phrases, or individual text characters) to be visually presented to the human subject, superficial aspects of the message that may be augmented at 612 may include font, typeface, text size, text color, highlighting, bolding, italics, kerning, etc., among other suitable non-semantic, non-rule violating features. For text-based message components (e.g., words, phrases, or phonetic) to be audibly presented to the human subject, superficial aspects of the message that may be augmented at 612 may include a volume of the voice or speaker, an accent of the voice or speaker, an enunciation, etc. It will be understood that these examples are to be considered non-limiting as other suitable superficial aspects of the information-bearing messages may be augmented to elicit an instance of the ERP-P3b component.

Within the context of eliciting an instance of the ERP-P3b component, the message components (e.g., letters, words, phonetics, phrases, etc.) that are augmented at 614 typically represent less than half of the message within the visual or auditory domain. Given that the magnitude of the deflection of the ERP-P3b waveform is typically greater with respect to less frequent/less dense superficial oddball events within a given message, it may be sufficient and even beneficial to introduce infrequent superficial oddball features into the message by augmenting an individual letter, word, phonetic, or phrase within a much larger message containing many letters, words, phonetics, or phrases.

In at least some implementations, the HMD device or HMD system may programmatically augment superficial aspects of an information-bearing message using a pre-defined rule set. For example, this rule set may define the inclusion of a superficial oddball stimulus within information-bearing message(s) at a pre-defined frequency or at random intervals within bounded domains (e.g., not greater than one superficial oddball stimulus per 10 sentences/messages, and not less than one superficial oddball stimulus per 20 sentences/messages). Furthermore, this rule set may define which superficial aspects (i.e., modality) of the messages may be augmented and/or the frequency of use of each modality. Further still, feedback from ERP-P3b detection (e.g., at 620, 622) from ERP responses by the human subject may be used to increase or decrease the frequency of such superficial augmentation to thereby ensure sufficiently strong ERP-P3b waveforms are generated by the human subject for detection.

At 616, the method includes presenting a stimulus to the human subject. Within the context of eliciting an instance of the ERP-P3b component, the augmented set of information-bearing messages obtained at 614 may be presented to the human subject in visual and/or auditory form. If a particular message is to be visually presented to the human subject (i.e., a visual stimulus), the message may be visually presented via a graphical display of the HMD device or a peripheral device interfacing with the HMD device or HMD system. If a particular message is to be audibly presented to the human subject (i.e., an auditory stimulus), the message may be audibly presented via an audio speaker of the HMD device or a peripheral device interfacing with the HMD device or HMD system.

As part of operation 616, a stimulus-time value representing a time at which the stimulus event was presented to the human subject may be logged to enable time-locking of EEG signals for the subsequent detection of ERPs. Within the context of an auditory stimulus event, the stimulus-time value may be logged at a time when the relatively infrequent auditory stimulus introduced into the message at operation 614 (e.g., an augmented word, phonetic, phrase, etc.) is presented via the audio speaker (e.g., spoken aloud). Within the context of a visual stimulus event, the stimulus-time value may be logged at a time when the relatively infrequent visual stimulus introduced into the message at operation 614 (e.g., an augmented letter, word, phrase, etc.) is presented via a graphical display device. Optionally, a predefined amount of delay may be added to the time of visual presentation to account for reading-based latency. This pre-defined amount of delay may be determined by the HMD system based on a relative location of the infrequent visual stimulus within the message and a typical reading speed of the human subject (specifically) or a generalized reading speed of a population of users to thereby provide a more likely stimulus-time within reading-based environments.

At 618, the method includes obtaining a set of one or more EEG signals via a set of one or more EEG interfaces. The set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, sampling, and storing or otherwise buffering the signal information in a data storage device (e.g., as sampled data). In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 620, the method includes processing one or more of the EEG signals to detect an ERP-P3b waveform. As previously described with reference to FIG. 5, an EEG signal for detecting an ERP-P3b waveform may be obtained via at least one EEG interface having an electrode that observes the temporal-parietal regions of the head of the human subject, as a non-limiting example. The ERP-P3b waveform may be detected within an ERP-P3b search window of the EEG signal approximately 250-500 ms following onset of the stimulus event presented at operation 616. In at least some implementations, the largest amplitude of a positive deflection occurring within this ERP-P3b search window may be identified as the peak of the ERP-P3b waveform. The ERP-P3b waveform may be sampled, stored, and analyzed as sub-processes to operation 530.

Following detection of the ERP-P3b waveform, a waveform profile may be established in a database system that represents an association between or among a variety of information relating to the waveform event. As a non-limiting example, an association may be established between some or all of the following information with regards to a detected ERP-P3b waveform: (1) a waveform event identifier that is sufficiently unique within a domain to enable a particular instance of a detected ERP waveform to be distinguished from other instances of detected ERP waveforms with respect to the human subject and/or among other human subjects of a group, (2) sampling data obtained from the EEG signal representing the waveform and/or data surrounding the waveform within a buffer region (e.g., voltage values vs. time values describing the waveform), (3) baseline data obtained from the EEG signal representing a baseline voltage prior to onset of the stimulus and/or between onset of the stimulus and the beginning of the waveform deflection, (4) a peak-amplitude value (e.g., maximum voltage value) at the peak of the waveform (e.g., measured relative to the baseline or other reference value), (5) a peak-time value at the peak of the waveform (e.g., measured relative to the onset of stimulus event) or other suitable measure of latency of the waveform in relation to onset of the stimulus event, (6) a trial number for the stimulus event within a set of stimulus events presented to the human subject during the current session for eliciting the ERP-P3b component and/or across all sessions for the human subject, (7) a wavelength or time-based measurement of the waveform within the time domain, (8) an average magnitude or integral of the waveform, (9) a measurement of the degree of symmetry of the waveform about the peak-amplitude value within the voltage and/or time domains, among other suitable data. However, if an ERP-P3b waveform was not detected at 620, the method may proceed to operation 640, whereby the human subject may be identified as having the lowest level of attentiveness corresponding to a complete lack of attention to the stimulus presented at 616.

At 622, the method includes determining one or more measurements of the ERP-P3b waveform, which may be based on a comparison to a P3b-baseline. As a non-limiting example, the one or more measurements of the ERP-P3b waveform may include or may be based on a combination of measurements obtained at operation 620, including (1) the peak-amplitude value (e.g., maximum voltage value) at the peak of the waveform (e.g., measured relative to the baseline or other reference value), (2) the peak-time value at the peak of the waveform (e.g., measured relative to the onset of stimulus event) or other suitable measure of latency of the waveform in relation to onset of the stimulus event, (3) a trial number for the stimulus event within a set of stimulus events presented to the human subject during the current session for eliciting the ERP-P3b component and/or across all sessions for the human subject.

The P3b-baseline may be obtained at 632, and may include retrieving the P3b-baseline from a database system (e.g., a user profile) held on storage device of the HMD device or the HMD system. The P3b-baseline may be user-specific in at least some implementations. The P3b-baseline may be pre-defined and/or based on historic measurements of ERP-P3b waveforms with respect to the human subject or other subjects within a group of users. Historic measurements of ERP-P3b waveforms may be obtained during a training phase involving the human subject or other subjects, and/or during runtime within real-world implementations involving the human subject or other subjects. For example, individualized training of a classifier may be conducted at 630 for the human subject to establish the P3b-baseline. The P3b-baseline may be developed with respect to a particular set of operating conditions (e.g., time of day, context, task, stimulus, etc.) and/or human state (e.g., drowsy or non-drowsy, attentive or non-attentive, etc.). The individualized training of the classifier conducted at 630 may be over one or more prior sessions of the human subject interacting with the HMD device or HMD system in a variety of different contexts to establish the P3b-baseline. For example, the classifier may be trained for the human subject's specific variations in ERP-P3b waveform shape, distribution, and properties to establish an individualized baseline for a particular context. The individualized baseline for a relatively high level of attentiveness may be measured when the human subject is awake, paying attention to a task, and well rested.

The amplitude of the ERP-P3b waveform may depend on current cognitive workload of the human subject and can be used in comparison to recent ERP-P3b recordings in other contexts to establish levels of interference of the current task/location context of the human subject. When a human subject is exposed to a sequence of stimuli, some of which are superficially different than the others, an instance of the ERP-P3b component will be elicited in response to the unusual stimulus whose amplitude and delay of the resulting ERP-P3b waveform are dependent on the rarity of the stimulus, the age, gender, and genetics of the user, and their current state of sleepiness, cognitive workload, attentional capacity, and many more factors. While many ERP-P3b waveforms obtained over multiple trials with the human subject may be averaged together to improve signal-to-noise ratio, techniques such as single-layer perceptrons and wavelet-ICA may be applied to reach single-trial, single-channel classification with 85% accuracy.

At 640, the method includes determining a value representing a level of attentiveness of the human subject based on the one or more measurement(s) of the ERP-P3b waveform. If an ERP-P3b waveform was not identified or measured at operations 620 and/or 622, then a value representing a level of attentiveness of the human subject may be determined to be the value that corresponds to the lowest level of attentiveness (i.e., that the human subject is not paying attention to the stimulus). By contrast, if an ERP-P3b waveform was identified at operation 620, then the value determined at operation 640 may be based on the measurement of the ERP-P3b waveform determined at operation 622. ERP-P3b waveforms that more closely resemble historic ERP-P3b values indicative of the human subject being awake, paying attention, and well rested for a given set of operating conditions will be determined to have a value that represents a greater level of attentiveness than ERP-P3b waveforms that exhibit greater latency and/or lesser magnitude than the historic ERP-P3b values. In at least some implementations, the level of attentiveness of the human subject may be based on a plurality of measurements, such as the peak-amplitude, the peak-time, and the trial number of the stimulus event within the session, as a non-limiting example.

At 642, the method includes outputting the value representing the level of attentiveness of the human subject. This value may be one of a plurality of values within a domain of potential values representing respective levels of attentiveness. The domain of potential values may include a plurality of discrete values or a continuous range of values, each representing a respective level of attentiveness. For example, a domain of potential attentiveness levels may have at least two levels (i.e., binary) represented by two distinguishable values (e.g., 0,1) that correspond to a less attentive state and a more attentive state, respectively. Here, detection of a ERP-P3b waveform within a corresponding ERP-P3b search window following the stimulus event may correspond to a higher level of attentiveness whereas lack of a ERP-P3b waveform within the ERP-P3b search window following the stimulus event may correspond to a lower level of attentiveness. Three or more levels may be represented by respective values within the domain of potential values for attentiveness. For example, detection of a ERP-P3b waveform having a first set of measurements (e.g., a higher amplitude) within a corresponding ERP-P3b search window following the stimulus event may correspond to a higher level of attentiveness whereas detection of a ERP-P3b waveform having a second set of measurements (e.g., a lower amplitude) within a corresponding ERP-P3b search window following the stimulus event may correspond to a moderate level of attentiveness whereas lack of a ERP-P3b waveform within the ERP-P3b search window following the stimulus event may correspond to a lower level of attentiveness. Each pair of neighboring values for attentiveness within the domain of potential values may be delineated by a threshold, at least within the context of discrete values representing discrete levels of attentiveness.

At 644, the method includes programmatically performing one or more operations based on the level of attentiveness of the human subject. Examples of operations that may be programmatically performed by the HMD system are described in further detail with reference to FIG. 8. Method 600 or portions thereof may be performed periodically or at defined time intervals to obtain updated measurements of the human subject and determine an updated level of attentiveness associated with the human subject.

Figure 7:
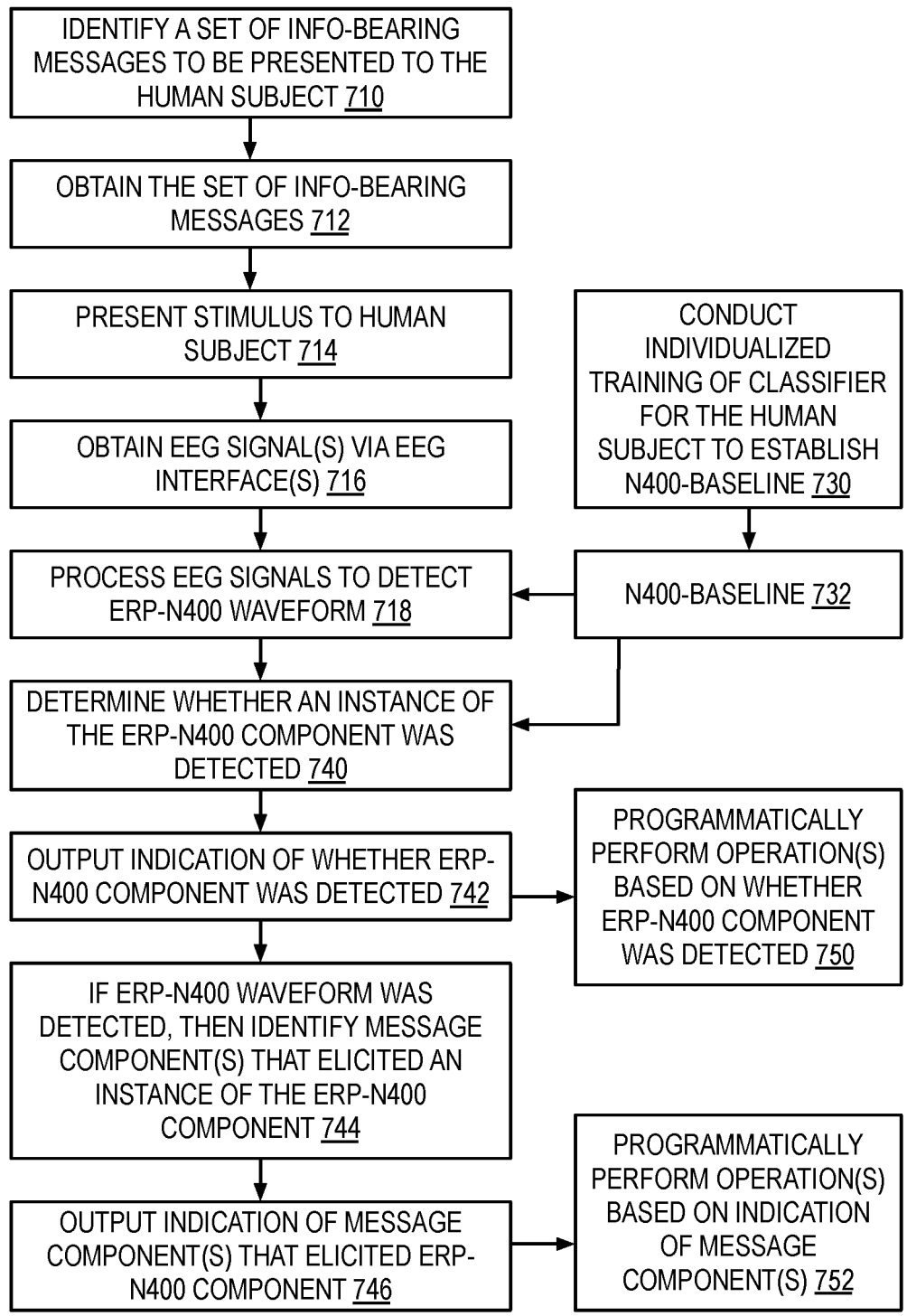
FIG. 7 is a flow diagram depicting an example method associated with message comprehension monitoring with respect to a human subject.

FIG. 7 is a flow diagram depicting an example method 700 associated with message comprehension monitoring with respect to a human subject. In at least some implementations, method 700 or portions thereof may be performed by a computing device located on-board an HMD device. Alternatively or additionally, portions of method 700 may be performed off-board the HMD device by one or more off-board computing devices of the HMD system. Furthermore, in at least some implementations, method 700 or portions thereof may be performed in real-time, and during runtime of the HMD device with respect to the human subject as a user of the HMD device. However, in other implementations, portions of method 700 may be performed in a post-processing operation that is not necessarily in real-time or during runtime of the HMD device. Method 700 may be performed in combination with methods 500 and/or 600 of FIGS. 5 and 6 to achieve more robust monitoring of drowsiness, attention, and comprehension with respect to a human subject.

At 710, the method includes identifying a set of information-bearing messages to be presented to the human subject. This set of messages may be identified for a given context of the user (i.e., the human subject) and/or client device (e.g., the HMD device) within an active session, which may be based on the operating conditions and/or the operating mode identified by the HMD system. The set of messages may include one or more information-bearing messages. Such messages may be generated by the HMD system or the HMD device, or may be received from a third-party device.

At 712, the method includes obtaining the set of information-bearing messages. Each information-bearing message of the set of message may include one or more human-perceivable sentences, sentence fragments, phrases, or words that contain text-based information reproducible in either visual or auditory form. Each message may be obtained by retrieving the message from a data storage device or receiving the message from another device over a communications network.

At 714, the method includes presenting a stimulus to the human subject. Within the context of eliciting an instance of the ERP-N400 component, the set of information-bearing messages obtained at 612 may be presented to the human subject in visual and/or auditory form. If an information-bearing message is to be audibly presented to the human subject as an auditory stimulus, the message may be audibly presented via an audio speaker of the HMD device or a peripheral device interfacing with the HMD device or HMD system. For example, the information-bearing message may be presented in spoken form by a human or by a synthesized voice. The message may be contained within a pre-recorded audio file, may be generated in real-time (e.g., for a synthesized voice), or may take the form of a live message (e.g., for real-time communications involving a human voice). If an information-bearing message is to be visually presented to the human subject as a visual stimulus, the message may be visually presented via a graphical display device of the HMD device or a peripheral device interfacing with the HMD device or HMD system. For example, an information-bearing message may be presented as text characters forming words, phrases, and/or sentences within an individual image frame or may be broken into multiple image frames that are sequentially presented via the graphical display device.

As part of operation 714, a stimulus-time value may be logged that represents a time at which the stimulus was presented to the human subject. In at least some implementations, the stimulus-time value may correspond to a time at which presentation of the information-bearing message was initiated. However, given that human language naturally relies upon time-based, sequential presentation and/or comprehension of phonetics, words, phrases, sentences, etc. to convey and comprehend an information-bearing message, the stimulus-time value may correspond to a time that is subsequent to the time at which presentation of the information-bearing message was initiated.

In the context of audible messages, each message component, such as each phonetic, word, phrase, sentence, etc. may correspond to a respective stimulus-time value that may be logged at the time of presentation, or such message components may be keyed to a preceding stimulus-time value (e.g., the start of the audible message) to enable their time of presentation to be determined from the preceding stimulus-time value. For example, a message that includes a ten word sentence that is audibly presented may have a stimulus-time value that corresponds to a time of presentation of the fourth word of the sentence. As another example, a message that includes a ten word sentence that is audibly presented may have a stimulus-time value that corresponds to a time that the first word of the sentence was audibly presented, and each subsequent word of the sentence may occupy a respective pre-defined time span that follows in sequence from the stimulus-time value, thereby enabling a stimulus-time value for the fourth word of the sentence to be identified.

In the context of visual messages, each message component, such as each word, phrase, sentence, etc. may be presented via a different image frame, depending on a level of desired resolution for attributing an instance of the ERP-N400 component to a particular message component. As a first example, each sentence of a multi-sentence message may be visually presented via a respective image frame. As a second example, each word of a multi-word message may be visually presented via a respective image frame of a multi-frame sequence. This second example may provide greater resolution with respect to identifying which word of the sentence elicited an instance of the ERP-N400 component. As previously described with reference to audible message components, image frames containing visual message components may be presented at a pre-defined rate that enables a stimulus-time to be identified for a particular image frame. For example, a message that includes a ten word sentence that is visually presented as ten sequential image frames of pre-defined duration may have a stimulus-time that corresponds to a time of presentation of the first image frame of the sentence, and a stimulus-time for each subsequent image frame of the sequence may be determined from the pre-defined duration of each preceding image frame. As another example, each image frame of a sequence may be associated with its own respective stimulus-time, enabling the stimulus-time of a particular image frame to be logged or otherwise identified.

In at least some implementations, a particular message component (e.g., phonetic, word, phrase, sentence, etc.) may be included within a message for the purpose of eliciting an instance of the ERP-N400 component. Here, the message component may be known prior to detection of the ERP-N400 component. In this implementation, the stimulus-time may correspond to a time at which that message component is presented to the human subject, either visually or audibly.

Method 700 may optionally include an operation performed prior to presentation of the stimulus in which a semantic oddball message component is added into the message for the purpose of eliciting the ERP-N400 component. This operation may be similar to previously described operation 614 of FIG. 6 with the exception that an entire word or phrase may be semantically augmented in the context of the ERP-N400 component rather than the superficial augmentation used to elicit the ERP-P3b component. Furthermore, methods 600 and 700 may performed in combination with each other or concurrently on the same information-bearing message to elicit both ERP-P3b and ERP-N400 components, thereby enabling a level of attentiveness and a level of message comprehension to be determined with respect to the same stimulus or set of stimuli.

At 716, the method includes obtaining a set of one or more EEG signal(s) via a set of one or more EEG interface(s). The set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, sampling, and storing or otherwise buffering the signal information in a data storage device (e.g., as sampled data). In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 718, the method includes processing one or more of the EEG signals to detect an ERP-N400 waveform, which may be based on a comparison of the EEG signal to an N400-baseline. As a non-limiting example, the one or more measurements of the ERP-N400 waveform may include or may be based on a combination of measurements, including (1) the peak-amplitude value (e.g., maximum voltage value) at the peak of the waveform (e.g., measured relative to the baseline or other reference value), (2) the peak-time value at the peak of the waveform (e.g., measured relative to the onset of stimulus event) or other suitable measure of latency of the waveform in relation to onset of the stimulus event, (3) a trial number for the stimulus event within a set of stimulus events presented to the human subject during the current session for eliciting the ERP-N400 component and/or across all sessions for the human subject. However, other voltage and/or time-based measurements of the waveform may be obtained as part of operation 718.

The N400-baseline may be obtained at 732, and may include retrieving the N400-baseline from a database system (e.g., a user profile) held on storage device of the HMD device or the HMD system. The N400-baseline may be user-specific in at least some implementations. The N400-baseline may be pre-defined and/or based on historic measurements of ERP-N400 waveforms with respect to the human subject or other subjects within a group of users. Historic measurements of ERP-N400 waveforms may be obtained during a training phase involving the human subject or other subjects, and/or during runtime within real-world implementations involving the human subject or other subjects. For example, individualized training of a classifier may be conducted at 730 for the human subject to establish the N400-baseline. The N400-baseline may be developed with respect to a particular set of operating conditions (e.g., time of day, context, task, stimulus, etc.) and/or human state (e.g., drowsy or non-drowsy, attentive or non-attentive, high comprehension or low comprehension, etc.). The individualized training of the classifier conducted at 730 may be over one or more prior sessions of the human subject interacting with the HMD device or HMD system in a variety of different contexts to establish the N400-baseline. For example, the classifier may be trained for the human subject's specific variations in ERP-N400 waveform shape, distribution, and properties to establish an individualized baseline for a particular context. The individualized baseline for a relatively high level of comprehension may be measured when the human subject is known to be in a particular state or set of operating conditions.

At 740, the method includes determining whether an instance of the ERP-N400 component was detected. At 742, the method includes outputting an indication of whether the ERP-N400 component was detected. At 750, the method includes programmatically performing one or more operation(s) based on whether the ERP-N400 component was detected. At 744, the method includes, if an ERP-N400 waveform was detected, then identifying one or more message component(s) that elicited an instance of the ERP-N400 component. At 746, the method includes outputting an indication of the one or more message component(s) identified at 744 to have elicited an instance of the ERP-N400 component. At 748, the method includes programmatically performing one or more operation(s) based on the indication of the message component(s) identified as having elicited an instance of the ERP-N400 component. Method 700 or portions thereof may be performed periodically or at defined time intervals to obtain updated measurements of the human subject and determine an updated level of comprehension associated with the human subject.

Following detection of the ERP-N400 waveform, a waveform profile may be established in a database system that represents an association between or among a variety of information relating to the waveform event. As a non-limiting example, an association may be established between some or all of the following information with regards to a detected ERP-N400 waveform: (1) a waveform event identifier that is sufficiently unique within a domain to enable a particular instance of a detected ERP waveform to be distinguished from other instances of detected ERP waveforms with respect to the human subject and/or among other human subjects of a group, (2) sampling data obtained from the EEG signal representing the waveform and/or data surrounding the waveform within a buffer region (e.g., voltage values vs. time values describing the waveform), (3) baseline data obtained from the EEG signal representing a baseline voltage prior to onset of the stimulus and/or between onset of the stimulus and the beginning of the waveform deflection, (4) a peak-amplitude value (e.g., maximum voltage value) at the peak of the waveform (e.g., measured relative to the baseline or other reference value), (5) a peak-time value at the peak of the waveform (e.g., measured relative to the onset of stimulus event) or other suitable measure of latency of the waveform in relation to onset of the stimulus event, (6) a trial number for the stimulus event within a set of stimulus events presented to the human subject during the current session for eliciting the ERP-N400 component and/or across all sessions for the human subject, (7) a wavelength or time-based measurement of the waveform within the time domain, (8) an average magnitude or integral of the waveform, (9) a measurement of the degree of symmetry of the waveform about the peak-amplitude value within the voltage and/or time domains, among other suitable data. However, if an ERP-N400 waveform was not detected at 742, the method may proceed to operation 750, whereby the human subject may be identified as having the lowest level of comprehension with respect to the stimulus presented at 714.

For information-bearing messages that are visually presented with many concurrent message components within an individual image frame, a predefined amount of delay may be added to the time of visual presentation to account for reading-based latency. This predefined amount of delay may be determined by the HMD system based on a relative location of the infrequent visual stimulus within the message and a typical reading speed of the human subject (specifically) or a generalized reading speed of a population of users to thereby provide a more likely stimulus-time within reading-based environments.

The combination of detection and analyses of the ERP-N400 component as described with reference to FIG. 7 and the ERP-P3b component as described with reference to FIGS. 5 and 6 allow for increased certainty that the reason for a lack of an ERP-N400 component in response to a stimulus was not due to the message going unattended by the human subject. Accordingly, the same message may be used in an attempt to elicit both ERP-P3b and ERP-N400 components from a human subject.

Figure 8:
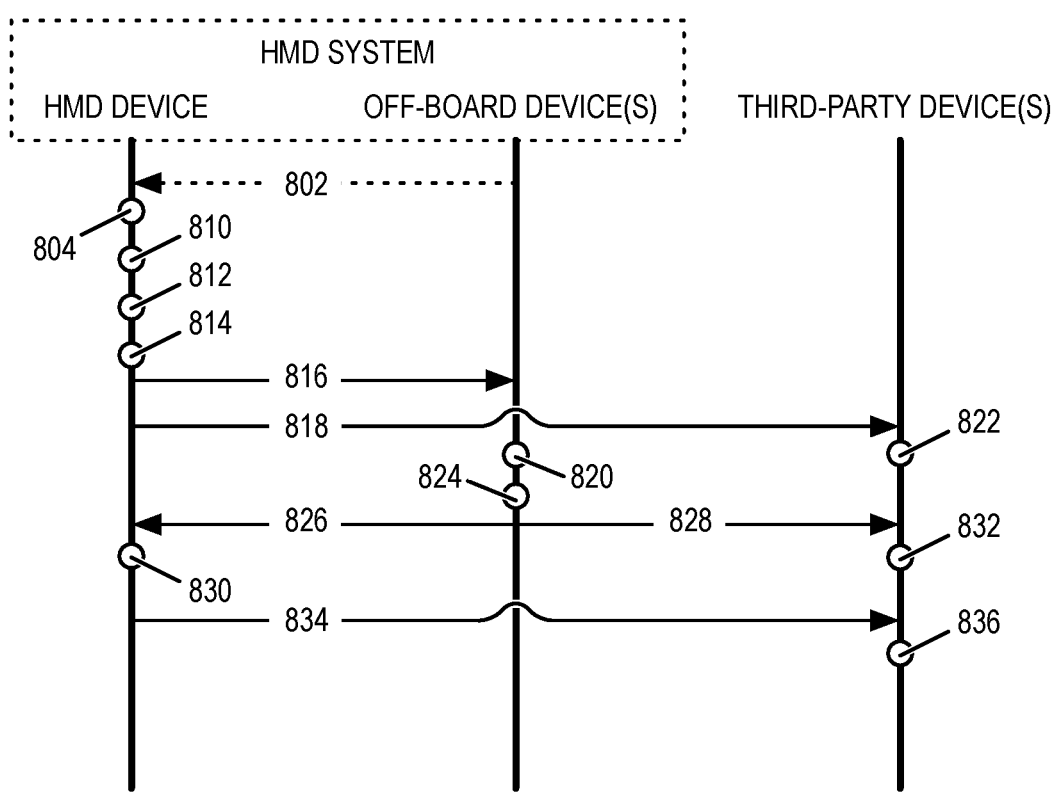
FIG. 8 is a diagram depicting example interactions between an HMD device, off-board device(s) of an HMD system, and third-party device(s) that are external the HMD system.

FIG. 8 is a diagram depicting example interactions between an HMD device, off-board device(s) that form part of an HMD system in combination with the HMD device, and third-party device(s) that are external the HMD system. Here, the HMD device, the off-board device(s), and the third-party device(s) of FIG. 8 are non-limiting examples of previously described HMD device 110, off-board device(s) 114, and third-party device(s) 140 of FIG. 1, respectively. The HMD system of FIG. 8 is a non-limiting example of previously described HMD system 112 of FIG. 1.

At 810, EEG signals may be obtained by the HMD device via a set of one or more EEG interfaces. The EEG signals may represent observations of the brain activity of a human subject, and may indicate one or more ERPs. The ERPs may be generated in response to a stimulus event. In some examples, the stimulus event may include or result from a visual, auditory, and/or haptic stimulus output by the HMD device or HMD system, as indicated at 804. This stimulus may be generated on-board the HMD device or may be generated in response to a command communicated by off-board devices or third-party to the HMD device, as indicated at 802. The HMD device may output a visual stimulus via a graphical display device of the HMD device or a peripheral device of the HMD device or HMD system, an auditory stimulus via an audio speaker of the HMD device or a peripheral device of the HMD device or HMD system, and/or a haptic stimulus via a haptic device of the HMD device or a peripheral device of the HMD device or HMD system.

In at least some implementations, the EEG signals may be processed at the HMD device to locally detect an ERP and/or ERP components, as indicated at 812. At 814, the HMD device may programmatically perform one or more operations responsive to detecting the ERP and/or ERP components. As an example of an operation that may be programmatically performed by the HMD device, at 816, the HMD device may communicate an indication of a detected ERP or ERP component to one or more off-board device(s) that collectively form part of the HMD system. Alternatively or additionally, as indicated at 818, the HMD device may communicate an indication of the detected ERP or ERP component to one or more third-party device(s). These communications may be transmitted and received over a communications network. An indication of a detected ERP or ERP component may include or may be accompanied by event-associated information, as will be described in further detail below.

In at least some implementations, an indication of a detected ERP may include or take the form of an ERP identifier that identifies the specific instance of the detected ERP. This ERP identifier may include or may be based on a global time value of detection of the ERP, a user identifier for the human subject from which the ERP was observed, a hardware identifier for the HMD device by which the ERP was observed, a relative position of the ERP within a sequence of ERPs observed by the HMD device, a program context within which the ERP was detected, etc. Furthermore, an identifier for each of the detected ERP components of the ERP may be included with or form part of the indication of the ERP. For example, an ERP may include ERP components such as ERP-P3b, ERP-N400, etc. that were detected within the EEG signals in response to the same stimulus event. Each of these ERP components may be represented by a respective ERP component identifier that enables multiple ERP components of an ERP to be identified and distinguished from each other based on their respective identifiers. Furthermore, ERP components detected with respect to a particular ERP may be identified based on an association of corresponding ERP component identifiers with the corresponding ERP identifier.

At 820, the off-board device(s) may receive the indication of the detected ERP and/or ERP components communicated by the HMD device at 816, and may programmatically perform one or more operations responsive to the indication. Alternatively or additionally, at 822, the third-party device(s) may receive the indication of the detected ERP and/or ERP components communicated by the HMD device at 818, and may programmatically perform one or more operations responsive to the indication.

In at least some implementations, EEG signal information obtained at 810 may be instead communicated at 816 by the HMD device to the off-board device(s) for processing. The off-board device(s) may receive and process the EEG signal information to detect the ERP and/or ERP components at 820. At 824, the off-board device(s) may programmatically perform one or more operations responsive to detecting the ERP and/or ERP components. For example, the off-board device(s) may communicate an indication of the detected ERP and/or ERP components to the HMD device at 826. Alternatively or additionally, the off-board device(s) may communicate an indication of the detected ERP and/or ERP components to the third-party device(s) at 828.

At 830, the HMD device may receive the indication of the detected ERP and/or ERP components communicated by the off-board device(s) at 826, and may programmatically perform one or more operations responsive to the indication. Alternatively or additionally, at 832, the third-party device(s) may receive the indication of the detected ERP and/or ERP components communicated by the off-board device(s) at 828, and may programmatically perform one or more operations responsive to the indication. For example, as indicated at 834, the HMD device may communicate an indication of the detected ERP and/or ERP components to the third-party device(s). At 836, the third-party device(s) may receive the indication of the detected ERP and/or ERP components communicated by the HMD device at 834, and may programmatically perform one or more operations responsive to the indication as indicated at 836.

FIG. 8 further depicts how off-board device(s) of the HMD system, such as remote sensors, may communicate information to the HMD device as depicted at 802. Examples of this information may include sensor information, such as user selections, user inputs, or other user monitoring data captured via sensor devices that are located off-board the HMD device. These user selections or user inputs may correspond to stimulus events that are observed by the user to elicit ERPs, for example. While FIG. 8 depicts communications initiated by a sender of the communicated information, in at least some implementations, this information may be instead requested from the sender by the receiving party, such as responsive to a user request or programmatically at predefined intervals or events.

In response to detecting an ERP/ERP component or receiving indication of a detected ERP/ERP component, some or all of the following operations may be performed by a computing device or computing system of the HMD device, the off-board device(s), and/or the third-party device(s): (1) storing an indication of the detected ERP/ERP component in a data storage device, (2) passing the indication of the detected ERP/ERP component to another process implemented by a computing device or computing system, (3) presenting or initiating presentation of the indicated ERP/ERP component via an output device to notify a user of the detected ERP/ERP component, (4) presenting or initiating presentation of a request for additional user input or performance of a user task via an output device, (5) transmitting or initiating transmission of the indicated ERP/ERP component directed to another computing device or computing system, (6) capturing a pre-defined data set that contains information to be associated with the detected ERP/ERP component, (7) associating information with an identifier of the ERP/ERP component to obtain event-associated data, (8) generating an event report for the detected ERP/ERP component that contains the event-associated data, (9) storing the event report and its event-associated data in a data storage device, (10) presenting or initiating presentation of the event report and its event-associated data via an output device, (11) transmitting or initiating transmission of the event report and its event-associated data directed to one or more subscriber(s) over a communications network, (12) transmitting or initiating transmission of a notification of the detected ERP/ERP component directed to one or more subscriber(s) over a communications network, (13) enabling one or more subscriber(s) to request and retrieve, or otherwise access the event report and its event-associated data from a data storage device for the ERP/ERP component.

In the above examples, the act of presenting or initiating presentation via an output device, may involve visual, auditory, and/or haptic output by one or more output device(s) of the HMD device, off-board device(s), and/or third-party device(s). For example, one or more graphical content items containing information perceivable by a user may be displayed via the graphical display(s) of the HMD device or other suitable graphical display device. As another example, a verbal message or other sound perceivable by a user may be generated via one or more audio speaker(s) of the HMD device or other suitable device.

Depending on implementation, some or all of the example operations described above may be programmatically performed by the HMD device, the off-board device(s), and/or the third-party device(s) responsive to detecting the ERP/ ERP component, or responsive to receiving indication of the detected ERP/ERP component, such as previously described with reference to operations 814, 820, 822, 824, 830, 832, 836, etc. Furthermore, the specific operation(s) performed in response to an ERP may be based on the ERP component(s) detected for that ERP, as well as the event-associated data.

With respect to ERP-P3b detection and drowsiness/attentiveness monitoring, operations that may be programmatically performed may include: (1) notifying the user or a supervisor of the user's drowsiness/attentiveness level(s) (e.g., if the drowsiness/attentiveness level(s) are below a threshold) to thereby provide the user with a warning as to their lack of attention or drowsiness, (2) offering to the user that the task be delayed if the drowsiness/attentiveness level(s) are below a threshold, (3) repeating or delaying a message if the drowsiness/attentiveness level(s) are below a threshold, requesting a user response delayed if the drowsiness/attentiveness level(s) are below a threshold, (4) testing and logging user drowsiness/attentiveness levels at periodic or predetermined intervals to enable real-time or subsequent analysis, user reflection, and micro-planning (i.e. effective time-dependent distribution of resources, workers, and their interactions for the best overall performance toward a collective goal). The HMD device or HMD system may use attentiveness level to programmatically implement a mode that seeks to ensure reception of messages by the users. Ensuring reception of a message may be achieved by one or more of the following: (1) unobtrusively pause the information display, and trigger a user heads-up display component (e.g., graphical element) that enables the user to selectively resume a stimuli, (2) offer to reschedule current reading or listening activities until the user is less drowsy or has more attention at a later time in the day (e.g., "mark as unread" and "remind me" within an application program such as email, calendar, etc.), (3) for high importance, time-critical messages—repeat the message until it is recognized as received, either through physical response (e.g., physical user input), responsive brain-computer interface, or by repeating information with stimulus variations until an appropriate P3b is observed. Consistently low attentiveness levels across many users for a given user interface or message may initiate a reorganization mode in which the AR system programmatically simplifies, cleans up, or otherwise reorganizes the user interface or messages. Alternatively or additionally, consistently low attentiveness levels across many users may be indicate to developers (as subscribers of the data) that the user interface or message should be simplified, cleaned up, or otherwise reorganized. For example, augmented/mixed reality graphical elements leftover from previous activities may be removed from the augmented/mixed reality view presented to the user via a graphical display device of the HMD device. Monitoring attentiveness and drowsiness across groups of users may enable detailed analysis of workers and improve worker efficacy over long timeframes. From a work planning perspective, tasks, calendar events, communications, physical locations, etc. may be marked as having high attentional/ awareness demands, allowing preemptive estimation of attentional demand of similar situations entailing events, communications, locations, etc. with tasks expected to require attention being automatically displayed during situations with low attentional demands and delayed during high attentional demand situations. User attentiveness level may be tracked for its daily variation due to Circadian rhythm so work-related tasks can be better scheduled according to their estimated instantaneous maximum attentional capacity or such that the current level of attention of the user exceeds a threshold level for a particular task.

With respect to ERP-N400, a missing ERP-N400 component following a stimulus event (indicative of lack of comprehension) may trigger the presentation of verification questions to the user to re-emphasize the potentially confusing point. ERP-N400 presence/absence may be tracked in order to provide a metric of user "cognitive adaptability". Specifically, if in an individual user ERP-N400s are reliably absent, it may indicate the user has difficulty understanding the typical messages that are presented to the user. This may possibly be due to a language or vocabulary barrier of the user, or a lack of relevant training and familiarity of terms contained in the message. This ERP-N400 presence/absence analysis may provide an indicator of the need for additional training, whether in work-sponsored language classes or supplemental training sessions with respect to particular users. In at least some implementations, the same message (i.e., stimulus event) may presented to multiple users (e.g., as may happen in an update indicating a change in procedure associated with a task). If multiple users show an ERP-N400 that was not a-priori expected in response to the same word or phrase, this may indicate unintended ambiguity or lack of clarity in the message, or a disconnect between worker understanding of the situation and overseer characterization of the situation. This knowledge could then trigger feedback or reporting to the message author (e.g., as a subscriber) requesting a rewording or re-explanation of the relevant section of the message.

Figure 9:
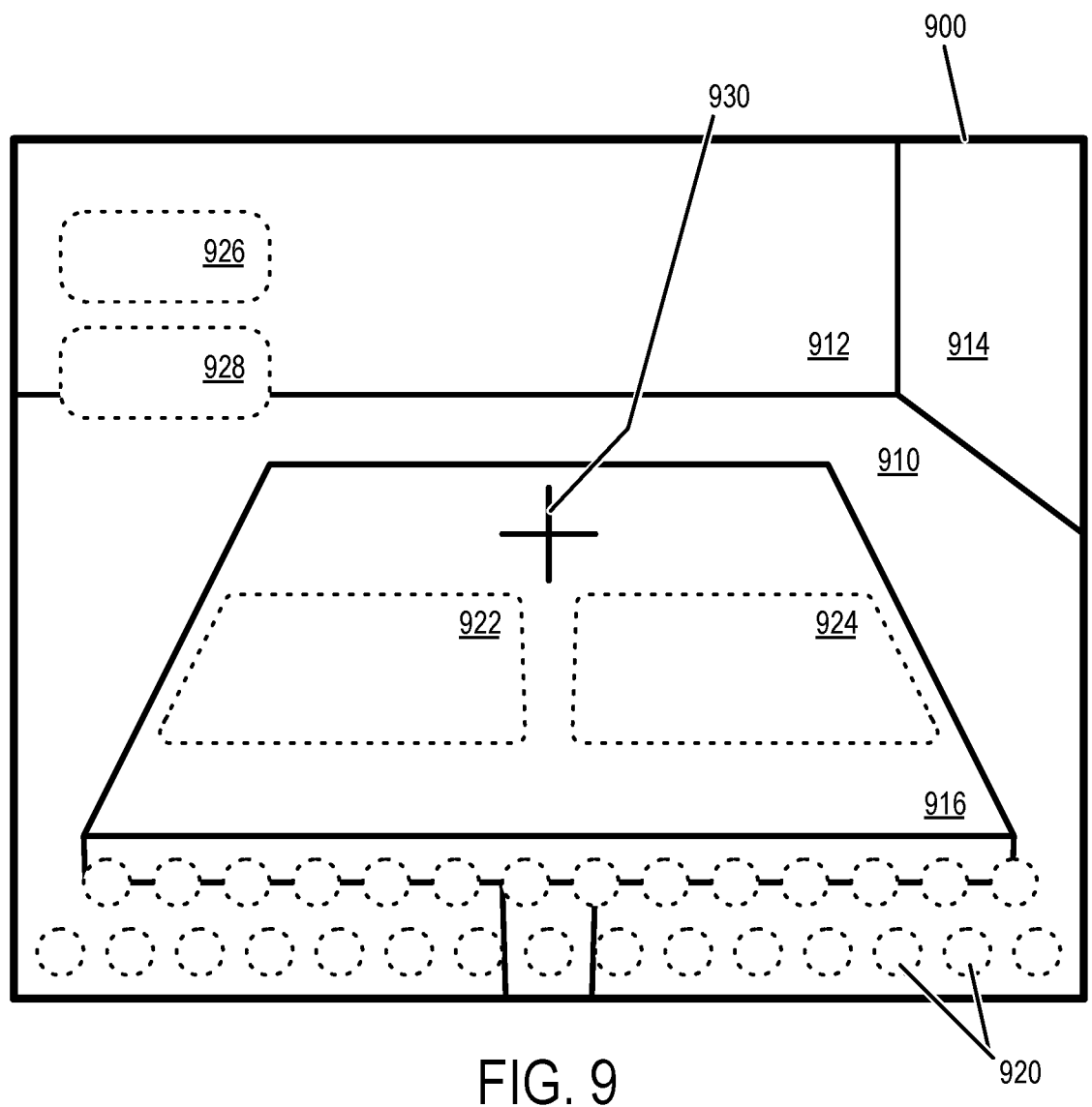
FIG. 9 depicts an example augmented reality or mixed reality view provided by an HMD device.

FIG. 9 depicts an example augmented reality or mixed reality view 900 that may be provided by an HMD device. Within view 900, physical objects that are present in the real-world environment may reside within a field of view of a user of the HMD device. In this example, a floor 910, walls 912 and 914, and a surface of a table 916 represent physical objects of the real-world environment that are present within the user's field of view. Also within view 900, one or more virtual objects may be presented via a graphical display device of the HMD device overlaid upon or integrated with the user's field of view of the real-world environment. In this example, virtual objects 920-928 (depicted in FIG. 9 with broken lines) are presented via a near-eye graphical display of the HMD device. These virtual objects take the form of visual augmented reality or mixed reality content when overlaid upon or integrated with the user's field of view of the real-world environment.

Some virtual objects may be world-locked, meaning that their positioning is defined by a particular positioning within the real-world environment. In this example, virtual objects 922, 924 are world-locked with respect to a surface of table 916 to provide the appearance that the virtual objects 922, 924 are resting upon the surface of the table. Some virtual objects may be view-locked, meaning that their positioning is tied to a particular positioning within the user's field of view that may be independent of an orientation of that field of view within the real-world environment. In this example, virtual objects 926, 928 are view-locked with respect to an upper left-hand corner region of the user's field of view, and a set of virtual objects 920 are view-locked with respect to a lower region of the user's field of view. The set of virtual objects 920 may, for example, represent a typing or spelling interface (e.g., a virtual keyboard) containing a plurality of alpha/numeric characters and/or related controls for generating human-readable text information.

Virtual objects, such as previously described virtual objects 920-928, may be presented by the HMD device as graphical elements that may include text, images, video, color, shading, textures, multi-dimensional models, menus, etc. Virtual objects may be two-dimensional or three-dimensional, static or dynamic, have a fixed position or may move relative to the user's field of view or real-world environment, depending on implementation or context. For example, a virtual object may take the form of a multi-dimensional graphical object (e.g., a two or three-dimensional object) having a six degree-of-freedom (6DOF) positioning (e.g., X, Y, Z values) and/or orientation (e.g., yaw, pitch, roll values) within a coordinate system within the user's field of view. Virtual objects may be selectable by a user to interact with the HMD device, the HMD system, or other suitable entity. Virtual objects, when graphically presented, may convey information that may be visually perceived by the user, such as through text information, color-coded information, imagery, etc. Such information may be context-specific and may be displayed, discontinued, updated, or otherwise varied in appearance by the HMD device based on context. For example, virtual objects may be selectively presented by the HMD device as visual stimulus that elicits ERPs from the user that may be detected by EEG interfaces located on-board the HMD device.

A virtual object presented via the HMD device may be targeted for selection by a user using a variety of techniques. Such techniques may include reticle-based targeting, eye tracking, and/or the use of peripheral pointing devices that interface with the HMD device. Non-limiting examples of these techniques are discussed in further detail below.

As a first example, a near-eye graphical display or see-through visor of the HMD device may include a reticle or other suitable sighting indicator (indicated schematically at 930) that aids the user in selection of graphical content presented via the HMD device. The reticle may take the form of a physical sighting indicator that is present upon or within a see-through graphical display or visor of the HMD device. In this implementation, the reticle as a physical sighting indicator is located at a fixed position that is view-locked to the user's field of view. Alternatively, the reticle may take the form of a graphical object presented via the graphical display of the HMD device, typically in a fixed position within the user's field of view in a view-locked implementation. The reticle, in combination with inertial sensors on-board the HMD device, may provide the user with the ability to target and select a virtual object that is presented via the HMD device or a physical object that is within the user's field of view. A dwell-based selection technique may be used enable the user to select the targeted object by aiming the reticle at the object, and maintaining that aim upon the object for at least a threshold period of time. Alternatively or additionally, an input device of the HMD device or a peripheral device interfacing with the HMD device may be used by the user to provide a selection command. Examples of such input devices include handheld devices that include a button or touch-sensitive input interface that may be actuated by the user to provide a selection command and/or a microphone on-board the HMD device by which a spoken selection command may be provided by the user.

As another example, eye tracking may be performed by the HMD device via an on-board ocular camera to determine a gaze vector of the user's eye. Eye tracking may be achieved using a variety of techniques. For example, an infrared (IR) light source located on-board the HMD device may emit IR that is projected upon the eye of the user. The IR may be used to illuminate features of the eye and/or produce a glint upon reflective surfaces of the eye, which may be captured by the ocular camera. A comparison of the relative positioning of these features of the eye and the reflected IR (e.g., glint) may be analyzed by the HMD device to identify or otherwise estimate a gaze vector of the user. In eye tracking implementations, the previously described reticle may be optionally omitted. A dwell-based selection technique may be used enable the user to select the targeted object by directing the user's gaze upon an object, and maintaining that gaze upon the object for at least a threshold period of time. A selection command may be generated with respect to an object in response to the user looking at the object, such that the user's gaze vector intersects the object, and in some implementations maintaining the gaze vector upon the object for at least a threshold period of time. Alternatively or additionally, an input device of the HMD device or a peripheral device interfacing with the HMD device may be used by the user to provide a selection command. Examples of such input devices include handheld devices that include a button or touch-sensitive input interface that may be actuated by the user to provide a selection command and/or a microphone on-board the HMD device by which a spoken selection command may be provided by the user.

As yet another example, a handheld device interfacing with the HMD device may take the form of a pointing device that enables a user to control a location of a selector icon (e.g., a pointer) presented via the graphical display of the HMD device. The selector icon may take the form of previously described sighting indicator 930, as an example. The handheld device may include one or more buttons, touch-sensitive interfaces, etc. In this implementation, the selector icon may move relative to the user's field of view in response to positioning commands provided by the user via the handheld device. Examples of pointing devices include a computer mouse, handheld controller, touch-sensitive interface, etc. Once an object has been targeted by the user moving the selector icon to the object, a selection command may be provided by the user to select that object. A selection command may be provided via the handheld device or other suitable user input device, such as a microphone as a spoken selection command.

FIG. 10 depicts an example head mounted display (HMD) device 1000 that is wearable upon a head of a human subject (i.e., a user). HMD device 1000 includes a device body 1010. Device body 1010, in this example, includes a helmet 1012 that is wearable by a user. Helmet 1012 includes a transparent or see-through visor 1014 that enables the user to view a real-world environment through the visor. However, HMD device 1000 may take other suitable forms, such as a headband, glasses, hat, or other suitable wearable form factor.

HMD device 1000 includes a see-through graphical display system 1040 (i.e., a see-through display) having one or more see-through display panels upon or within which computer-generated graphical content (e.g., one or more virtual objects) may be presented to a user while wearing the HMD device. Display subsystem 1040 is an example of a near-eye graphical display device that is mounted upon device body 1010 of the HMD device. In some examples, HMD device 1000 may include two or more see-through display panels or two or more independent display regions of a common see-through display panel, to provide independent graphical displays to each eye of the user.

In a first example, see-through graphical display system 1040 may include two side-by-side see-through display panels 1042 corresponding to a right eye and a left eye of the user. FIG. 10 depicts additional aspects of this example configuration. Alternatively a single see-through display panel 1042 may have two side-by-side display panel regions corresponding to a right eye and left eye of the user. See-through display panel(s) 1042 may include or take the form of reflective optical waveguides that receive light projected by one or more light projectors 1044, and reflect or otherwise direct at least a portion of that light towards the eyes of the user. For example, each display panel or display panel region thereof may receive light from a respective light projector. See-through display panel(s) 1042 may additionally or alternatively include or take the form of lenses that reflect or otherwise direct at least a portion of the light received from light projector(s) 1044 towards the eyes of the user.

In a second example, see-through graphical display system 1040 may omit see-through display panel(s) 1042, and one or more see-through display panels may be instead integrated into visor 1014. One or more display regions (indicated schematically at 1016) of visor 1014 may each include or take the form of a reflective optical waveguide that receives light projected by one or more light projector(s) 1044, and reflects that light back towards the eye or eyes of the user. The relative positioning of light projector(s) 1044 in FIG. 9 is represented schematically with respect to see-through display panel(s) 1042. As such, it will be understood that light projector(s) 1044 may reside at other suitable positions for projecting light onto or into see-through display panel(s) 1042, or alternatively onto or into see-through display region(s) 1016 of visor 1014.

A user, while wearing HMD device 1000, is permitted to view the real-world environment through the see-through display panel(s) of see-through graphical display system 1040. Graphical content, such as represented schematically at 1018 within the context of a visor-integrated see-through display panel, may optionally be presented by the HMD device. This graphical content may be sized and/or positioned relative to physical objects within the real-world environment to provide the appearance of the graphical content being physically present within the real-world environment. Alternatively or additionally, graphical content presented via the see-through graphical display may take the form of informational content that is not necessarily aligned with physical objects within the real-world environment.

HMD device 1000 may further include a variety of on-board sensors. As a non-limiting example, HMD device 1000 may include optical sensors, such as a forward facing camera 1050 and an ocular camera 1052. Forward facing camera 1050 may be configured and otherwise oriented to capture at least a portion of a field of view (some, all, or a greater field of view) of the user as the HMD device is worn upon the head of the user. Images or other optical sensor measurements captured by forward facing camera 1050 may be used by the HMD device, for example, to assist in aligning graphical content with physical features present within the real-world environment. Ocular camera 1052 may be oriented generally rearwards, towards an eye of the user. Images or other optical sensor measurements captured by ocular camera 1052 may be used by the HMD device, for example, to track a gaze direction of the user's eye or to otherwise measure features of the user's eye.

Additional on-board sensors include a set of spatially distributed EEG interfaces 1060, represented schematically in FIG. 10. Each EEG interface may include a non-invasive electrode that interfaces with a control subsystem of the HMD device via one or more wired electrical contacts. Electrodes 1062, 1064, and 1066 are depicted in FIG. 10, as examples of EEG interfaces 1060. Electrodes of EEG interfaces 1060 are typically located along an inner-facing surface of helmet 1012 or other wearable cap or band that covers at least a portion of the head of the user. In this example, HMD device 1010 includes a head strap 1032 that is adjustable to fit the size of the user's head, thereby providing a snug fit that brings the electrodes of the EEG interfaces into contact with or close proximity to a scalp or skin of the user.

While HMD devices are described herein within the context of see-through displays that provide a direct view of the real-world environment, it will be understood that the methods and techniques described herein may be implemented within the context of HMD devices that do not include a see-through display, but instead provide a live view of the real-world environment via an on-board camera (e.g., forward facing camera 150) and graphical display device.

FIG. 11 depicts additional aspects of an HMD device 1100. HMD device 1100 is a non-limiting example of previously described HMD device 1000 of FIG. 10. Within FIG. 11, HMD device 1100 is presented in a head-on view in contrast to the side view of HMD device 1000 depicted in FIG. 10. HMD device 1100 again takes the form of a helmet having a visor in this example. Here, a helmet 1102 of HMD device 1100 may include a variety of sensors such as forward facing camera 1108 and/or audio sensors 1110 (e.g., provided at the front, back, and/or a top section 1106 of helmet 1102). See-through display panels 1112 are separate from or independent of visor 1104 in this example, and are mounted to helmet 1102 via a body 1114. Helmet 1102 further includes rearward facing ocular cameras 1111 mounted thereon. Each ocular camera 1111 is directed to a respective eye of the user to capture an image of the iris, retina, pupil, or other eye components. Each ocular camera 1111 may be positioned on helmet 1102 above and/or to the side of each eye, and facing a corresponding eye. Helmet 1102 also includes a set of spatially distributed EEG interfaces 1160 to observe brain activity of the user, including non-invasive electrodes 1162, 1164, 1166, 1168, etc.

Figure 12:
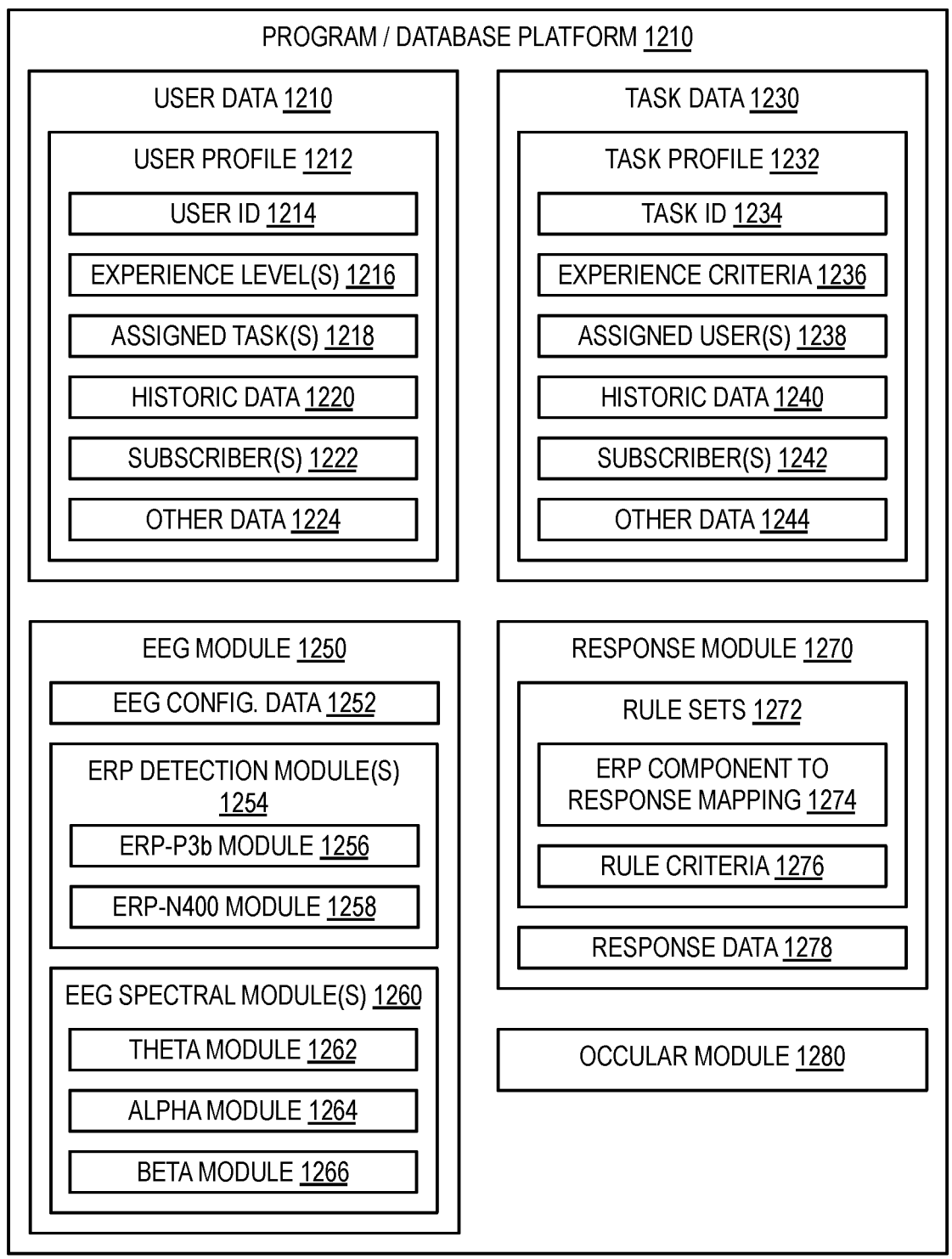
FIG. 12 is a schematic diagram depicting an example program/database latform.

FIG. 12 is a schematic diagram depicting an example program/database platform 1200. Platform 1200 may include computer executable instructions and/or data that may form one or more programs and/or database systems that are implemented by a computing device or computing system containing two or more computing devices. For example, platform 1200 may reside at an HMD device (or other client computing device) or may span two or more computing devices, such as an HMD device and one or more off-board device(s) of an HMD system.

In this example, platform 1200 includes user data 1210, task data 1230, EEG module 1250, and response module 1270. Typically, user data 1210 and task data 1230 are implemented as one or more databases of a database system stored at a data storage device. EEG module 1250 and response module 1270 are typically implemented as computer program components.

User data 1210 may include one or more user profiles corresponding to respective users of the platform. An example user profile 1212 for a particular user is depicted in FIG. 12. User profile 1212 includes a user identifier 1214, a set of skill level(s) 1216, a set of assigned task(s) 1218, historic data 1220, a set of subscriber(s) 1222, and other data 1224. User identifier 1214 refers to a particular user of the platform and enables that user to be distinguished from other users of the platform. The set of skill level(s) 1216 may include one or more skill levels that are associated with the user. In some examples, multiple skill levels may be assigned with the user in which each skill level pertains to a different task type or subject. Each skill level assigned to the user may be one of a plurality of assignable skill levels (e.g., novice or expert). The set of assigned task(s) 1218 may include one or more tasks that are associated with the users. These tasks may correspond to tasks that are defined by task data 1230. Historic data 1220 may include some or all data obtained by the platform with respect to the user, in raw and/or processed forms. The set of subscriber(s) 1222 may include one or more subscribers that are to receive reports, notifications, or other information updates relating to the user. Subscribers may include supervisors, administrators, the user itself, or other subscribers. Subscribers may be represented by a user name and/or contact address (email address, etc.) that enables and directs the platform to communicate information concerning the user to the subscriber.

Task data 1230 may include one or more task profiles corresponding to respective tasks that may be assigned to users of the platform. An example task profile 1232 for a particular task is depicted in FIG. 12. Task profile 1232 includes a task identifier 1234, a set of skill level criteria 1236, a set of assigned user(s) 1238, historic data 1240, a set of subscriber(s) 1242, and other data 1244. Task identifier 1234 refers to a particular task established by a supervisor, administrator, or other user of the platform, and enables that task to be distinguished from other tasks established for the platform. The set of skill level criteria 1236 may define to a minimum threshold skill level for users to be assigned to that task. As previously described, each skill level assigned to the user may be one of a plurality of assignable skill levels (e.g., novice or expert), and these skill levels may be defined on a per-task basis. The set of assigned user(s) 1238 may include one or more users (e.g., represented by user identifiers) that are associated with the tasks. These users may be defined within the platform and/or identified by user data 1210. Historic data 1240 may include some or all data obtained by the platform with respect to the task, in raw and/or processed forms. The set of subscriber(s) 1242 may include one or more subscribers that are to receive reports, notifications, or other information updates relating to the task. Subscribers may include supervisors, administrators, the user that initiated or performed the task, or other subscribers. As previously described, subscribers may be represented by a user name and/or contact address that enables and directs the platform to communicate information concerning the task to the subscriber.

EEG module 1250 includes EEG configuration data 1252, ERP detection module(s) 1254, and EEG spectral module(s) 1260. EEG configuration data 1252 includes data that defines a spatial relationship between or among the EEG interfaces of a particular hardware configuration. For example, EEG configuration data 1252 may define a spatial relationship for a set of EEG interfaces of an HMD device or other wearable device. The spatial relationship may be defined, at least in part, with reference to the previously described 10-20 system. However, other suitable frameworks may be used. In an example, each electrode of an EEG interface may be assigned an identifier that is further associated with a spatial positioning identifier that identifies a location relative to a head of human subject.

ERP detection module(s) 1254 includes one or more modules that are configured to detect a particular ERP component. For example, ERP detection module(s) 1254, to detect ERP components within a set of EEG signals, may include: ERP-P3b module 1256 to detect the ERP-P3b component, and ERP-N400 module 1258 to detect the ERP-N400 component, etc. In at least some implementations, ERP detection module(s) may be developed, at least in part, by training the ERP detection module(s) on EEG data for their respective ERP components using a set of EEG interfaces that corresponds to or is sufficiently similar in spatial configuration to the EEG interfaces (e.g., of an HMD device or other suitable wearable device) as described by EEG configuration data 1252. The various modules described herein may be implemented as a set of instructions that are executed or executable by logic devices of a computing device or computing system. Such modules may be stored in a data storage device of the computing device or computing system.

EEG spectral module(s) 1260 may include one or more modules that are configured to obtain and analyze a particular frequency range of an EEG signal. For example, EEG spectral module(s) 1260 may include a Theta module 1262 to obtain and analyze a Theta band of the EEG signals, an Alpha module 1264 to obtain and analyze an Alpha band of the EEG signals, a Beta module 1266 to obtain and analyze a Beta band of the EEG signal, etc.

Response module 1270 may include rule sets 1272 and response data 1278. Rule sets 1272 may include an ERP component to response mapping 1274 that directs the platform how to response to detection of particular ERP components. Rule sets 1272 may define the programmatic operations that are performed in response to detection of particular ERP components. Rule sets 1272 may further include rule criteria that defines trigger conditions for performing such programmatic operations. Response data 1278 may include information that defines the type of response and/or the content of that response. For example, response data 1278 may define whether a response includes visual, auditory, and/or haptic information, as well the content of the response. Program/database platform 1210 may further include an ocular module 1280 configured to obtain and analyze eye images captured of an eye of a human subject, and determine measurements of eye movement based on that analysis.

The various computing devices or computing systems described herein may incorporate one or more logic device (s), and one or more data storage device(s). A logic device includes one or more physical hardware devices configured to execute instructions. Such instructions are executable by the logic device to implement or otherwise perform the various methods or operations described herein. For example, a logic device may be configured to execute instructions that are part of one or more applications, services, programs, routines, libraries, objects, components, data structures, or other logical constructs. Such instructions may be implemented to perform a task or function, implement a data type, transform the state of one or more components, achieve a technical effect, or otherwise arrive at a desired result. A logic devices may include one or more processors configured to execute software instructions. Additionally or alternatively, a logic device may include one or more hardware or firmware logic machines configured to execute hardware or firmware instructions. Processors of a logic device may be single-core or multi-core, and the instructions executed thereon may be configured for sequential, parallel, and/or distributed processing. Individual components of a logic device may be distributed among two or more separate devices (e.g., an HMD device and an off-board device of an HMD system), which may be remotely located and/or configured for coordinated processing. Aspects of the logic device may be virtualized and executed by remotely accessible, networked computing devices configured in a cloud-computing configuration.

Data storage devices include one or more physical memory devices (e.g., non-transitory memory devices) configured to hold instructions executable by the logic devices to implement the methods or operations described herein. When such methods or operations are implemented, a state of the data storage devices may be transformed—e.g., to hold different data. Data storage devices may include removable and/or built-in devices. Data storage devices may include optical memory devices, semiconductor memory devices, and/or magnetic memory devices, among other suitable forms. Data storage devices may include volatile, nonvolatile, dynamic, static, read/write, read-only, random-access, sequential-access, location-addressable, file-addressable, and/or content-addressable devices.

Aspects of logic devices and data storage devices may be integrated together into one or more hardware-logic components. While a data storage device includes one or more physical hardware devices, aspects of the instructions described herein alternatively may be, at times, propagated by a communication medium (e.g., an electromagnetic signal, an optical signal, etc.) that is not held by a physical device for a finite duration.

It is to be understood that the configurations and/or approaches described herein are exemplary in nature, and that these examples are not to be considered in a limiting sense, because numerous variations are possible. The specific routines or methods described herein may represent any number of processing strategies. As such, the various acts illustrated may be performed in the sequence illustrated, in other sequences, in parallel, or in some cases omitted. Likewise, the order of the above-described processes may be changed without departing from the scope of the present disclosure.

The subject matter of the present disclosure includes all novel and nonobvious combinations and sub-combinations of the various processes, systems and configurations, and other features, functions, acts, and/or properties disclosed herein, as well as any and all equivalents thereof. It should be understood that the disclosed embodiments are illustrative and not restrictive. Variations to the disclosed embodiments that fall within the metes and bounds of the claims, now or later presented, or the equivalence of such metes and bounds are embraced by the claims.

The invention claimed is:

1. A computer-implemented method comprising:
    presenting, by one or more processors of a machine, a visual or auditory stimulus to a user of a head mounted device (HMD) worn on a head of the user, the HMD being configured to display augmented reality content in a transparent display of the HMD;
    obtaining, by one or more processors of the machine, a set of electroencephalography (EEG) signals via a set of EEG electrodes of the HMD, each EEG electrode being configured to detect fluctuations of an electrical potential at a corresponding location relative to the head of the user in response to the visual or auditory stimulus being presented;
    computing, by one or more processors of the machine, a level of drowsiness of the user based on the set of EEG signals; and
    determining, by one or more processors of the machine, the augmented reality content in response to a change in the level of drowsiness.

2. The computer-implemented method of claim 1, further comprising:
    generating a notification in response to the level of drowsiness transgressing a drowsiness threshold; and
    presenting the notification and an indication of the level of drowsiness in the transparent display of the HMD.

3. The computer-implemented method of claim 1, wherein the visual or auditory stimulus includes instructions, and the method further comprises:
    computing a level of comprehension of the instructions by the user based on the set of EEG signals; and
    adjusting the augmented reality content in response to the level of comprehension transgressing a comprehension threshold.

4. The computer-implemented method of claim 1, wherein the visual or auditory stimulus includes instructions, and the method further comprises:
    computing a level of attention of the user to the instructions based on the set of EEG signals; and
    adjusting the augmented reality content in response to the level of attention transgressing an attention threshold.

5. The computer-implemented method of claim 1, wherein the computing of the level of drowsiness comprises:
    detecting an event-related potential (ERP) in the user's response to presentation of the visual or auditory stimulus by searching within the set of EEG signals for at least one of:
        an ERP-P3b waveform having a positive deflection in electrical potential within an ERP-P3b time-based search window following the presenting of the visual or auditory stimulus, or
        an ERP-N400 waveform having a negative deflection in electrical potential within an ERP-N400 time-based search window following the presenting of the visual or auditory stimulus; and
    for each waveform present within the set of EEG signals, measuring a peak-amplitude value at a peak of that waveform and a peak-time value at the peak of that waveform relative to a time of presentation of the visual or auditory stimulus.

6. The computer-implemented method of claim 5, further comprising:
    communicating the level of drowsiness for the user with respect to the stimulus based on the measurements of the peak-amplitude and the peak-time value of the ERP-P3b waveform.

7. The computer-implemented method of claim 5, further comprising:
    communicating a level of attentiveness for the user with respect to the stimulus based on the measurements of the peak-amplitude and the peak-time value of the ERP-P3b waveform.

8. The computer-implemented method of claim 5, further comprising:
    communicating a level of comprehension for the user with respect to an information-bearing message of the stimulus based on the measurements of the peak-amplitude and the peak-time value of the ERP-N400 waveform.

9. The computer-implemented method of claim 1, further comprising:
obtaining time-based imagery of an eye of the user via an ocular camera of the head mounted device; and
obtaining measurements of eye movement with respect to the eye of the user by processing the time-based imagery;
wherein the computing of the level of drowsiness for the human subject is further based on the measurements of eye movement.

10. The computer-implemented method of claim 1, further comprising:
obtaining at least one of a Theta band, an Alpha band, or a Beta band; and
wherein the computing of the level of drowsiness for the user is further based on at least one of a measurement of amplitude or a regularity of frequency of the set of EEG signals within the one or more of the bands.

11. A head-mounted device (HMD) comprising:
a transparent display configured to display augmented reality content and present a visual stimulus to a user of the HMD worn on a head of the user;
a speaker configured to present an audio stimulus to the user of the HMD;
a set of EEG electrodes of the HMD, each EEG electrode configured to detect fluctuations of an electrical potential at a corresponding location relative to the head of the user of the HMD in response to the visual and auditory stimulus being presented;
a hardware processor configured to perform operations comprising:
obtaining a set of electroencephalography (EEG) signals via the set of EEG electrodes of the HMD;
computing a level of drowsiness of the user based on the EEG signals; and
adjusting the augmented reality content in response to a change in the level of drowsiness.

12. The HMD of claim 11, wherein the operations further comprise:
generating a notification in response to the level of drowsiness transgressing a drowsiness threshold; and
presenting the notification and an indication of the level of drowsiness in the transparent display of the HMD.

13. The HMD of claim 11, wherein the visual and auditory stimulus includes instructions, wherein the operations further comprise:
computing a level of comprehension of the instructions by the user based on the set of EEG signals; and
adjusting the augmented reality content in response to the level of comprehension transgressing a comprehension threshold.

14. The HMD of claim 11, wherein the visual or auditory stimulus includes instructions, wherein the operations further comprise:
computing a level of attention of the user to the instructions based on the set of EEG signals; and
adjusting the augmented reality content in response to the level of attention transgressing an attention threshold.

15. The HMD of claim 11, wherein computing the level of drowsiness comprises:

detecting an event-related potential (ERP) in the user's response to presentation of the visual or auditory stimulus by searching within the set of EEG signals for at least one of:
an ERP-P3b waveform having a positive deflection in electrical potential within an ERP-P3b time-based search window following the presenting of the visual or auditory stimulus, or an ERP-N400 waveform having a negative deflection in electrical potential within an ERP-N400 time-based search window following the presenting of the visual or auditory stimulus; and
for each waveform present within the set of EEG signals, measuring a peak-amplitude value at the peak of that waveform and a peak-time value at the peak of that waveform relative to a time of presentation of the visual or auditory stimulus.

16. The HMD of claim 15, wherein the operations further comprise:
communicating the level of drowsiness for the user with respect to the stimulus based on the measurements of the peak-amplitude and the peak-time value of the ERP-P3b waveform.

17. The HMD of claim 15, wherein the operations further comprise:
communicating a level of attentiveness for the user with respect to the stimulus based on the measurements of the peak-amplitude and the peak-time value of the ERP-P3b waveform.

18. The HMD of claim 15, wherein the operations further comprise:
communicating a level of comprehension for the user with respect to an information-bearing message of the stimulus based on the measurements of the peak-amplitude and the peak-time value of the ERP-N400 waveform.

19. The HMD of claim 11, wherein the operations further comprise:
obtaining one or more of a Theta band, Alpha band, and Beta band, in which each band corresponds to a respective frequency range of the set of EEG signals; and
wherein the level of drowsiness for the user is further based on a combination of a measurement of amplitude and a regularity of frequency of the set of EEG signals within the one or more of the bands.

20. A non-transitory machine-readable medium comprising instructions that, when executed by one or more processors of a machine, cause the machine to perform operations comprising:
presenting a visual or auditory stimulus to a user of a head mounted device (HMD) worn on a head of the user, the HMD being configured to display augmented reality content in a transparent display of the HMD;
obtaining a set of electroencephalography (EEG) signals via a set of EEG electrodes of the HMD, each EEG electrode being configured to detect fluctuations of an electrical potential at a corresponding location relative to the head of the user in response to the visual or auditory stimulus being presented;
computing a level of drowsiness of the user based on the set of EEG signals; and
determining the augmented reality content in response to a change in the level of drowsiness.

* * * * *